(12) United States Patent
Sun et al.

(10) Patent No.: US 7,113,821 B1
(45) Date of Patent: Sep. 26, 2006

(54) TISSUE ELECTROPERFORATION FOR ENHANCED DRUG DELIVERY

(75) Inventors: Ying Sun, Somerville, NJ (US); Ralph W. Oakeson, Racine, WI (US); Stephen J. Wisniewski, Doylestown, PA (US); Jonas C. T. Wang, West Windsor, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 09/644,093

(22) Filed: Aug. 23, 2000

Related U.S. Application Data

(60) Provisional application No. 60/150,636, filed on Aug. 25, 1999.

(51) Int. Cl.
*A61N 1/30* (2006.01)

(52) U.S. Cl. .......................... 604/21; 604/20; 604/500; 604/503; 604/509; 604/114; 604/96.01; 514/2; 514/54; 606/192; 606/193; 606/27; 606/28; 606/29; 606/31; 606/32; 606/41; 606/46; 606/47; 606/48; 606/49; 606/50; 606/191; 607/96; 607/101; 607/102; 607/113; 607/116; 607/178

(58) Field of Classification Search .................. 514/44, 514/54, 2, 12, 23; 436/147, 148–149; 604/20, 604/21, 500, 503, 509, 114, 96.01; 606/27–29, 606/31, 32, 91, 46–50, 191–193; 607/96, 607/101, 102, 117, 116, 138
See application file for complete search history.

(56) References Cited

U.S. PATENT DOCUMENTS

| | | | |
|---|---|---|---|
| 3,315,665 A | 4/1967 | MacLeod | 601/7 |
| 3,950,158 A | 4/1976 | Gossett | 62/4 |
| 3,964,482 A | 6/1976 | Gerstel et al. | 128/260 |
| 4,230,105 A | 10/1980 | Harwood | 128/156 |
| 4,406,658 A | 9/1983 | Lattin et al. | 604/20 |
| 4,655,766 A | 4/1987 | Theeuwes et al. | 604/896 |
| 4,685,911 A | 8/1987 | Konno et al. | 604/897 |
| 4,767,402 A | 8/1988 | Kost et al. | 604/22 |
| 4,790,824 A | 12/1988 | Morrow et al. | 604/143 |
| 4,963,360 A | 10/1990 | Argaud | 424/443 |
| 5,013,293 A | 5/1991 | Sibalis | 604/20 |

(Continued)

FOREIGN PATENT DOCUMENTS

| | | |
|---|---|---|
| DE | 195 25 607 A1 | 1/1997 |
| EP | 0 429 842 A2 | 6/1991 |
| GB | 2 303 208 A | 2/1997 |
| WO | 86/07269 A1 | 12/1986 |
| WO | 92/07618 A1 | 5/1992 |

(Continued)

OTHER PUBLICATIONS

Banga et al., Assessing the potential of skin electroporation for the delivery of protein- and gene-based drugs, 1998, Tibtech, vol. 16, pp. 408–412.*

Verma et al., Gene therapy– promises, problems and prospects, 1997, Nature, vol. 3879, pp. 239–242.*

Anderson, Human gene therapy, 1998, Nature, vol. 392, pp. 25–30.*

(Continued)

*Primary Examiner*—Nicholas D. Lucchesi
*Assistant Examiner*—Matthew F. DeSanto
(74) *Attorney, Agent, or Firm*—William E. McGowan

(57) ABSTRACT

The present invention relates to a method and a device for transporting a molecule through a mammalian barrier membrane of at least one layer of cells comprising the steps of: ablating the membrane with an electric current from a treatment electrode; and utilizing a driving force to move the molecule through the perforated membrane.

18 Claims, 12 Drawing Sheets

U.S. PATENT DOCUMENTS

| | | | | |
|---|---|---|---|---|
| 5,019,034 A | * | 5/1991 | Weaver et al. | 604/20 |
| 5,036,861 A | | 8/1991 | Sembrowich et al. | 128/763 |
| 5,042,975 A | | 8/1991 | Chien et al. | 604/20 |
| 5,135,478 A | | 8/1992 | Sibalis | 604/20 |
| 5,156,591 A | | 10/1992 | Gross et al. | 604/20 |
| 5,213,568 A | | 5/1993 | Lattin et al. | 604/20 |
| 5,224,927 A | | 7/1993 | Tapper | 604/20 |
| 5,250,023 A | | 10/1993 | Lee et al. | 604/20 |
| 5,279,543 A | | 1/1994 | Glikfeld et al. | 604/20 |
| 5,279,544 A | | 1/1994 | Gross et al. | 604/20 |
| 5,320,607 A | | 6/1994 | Ishibashi | 604/115 |
| 5,362,307 A | | 11/1994 | Guy et al. | 604/20 |
| 5,386,837 A | | 2/1995 | Sterzer | 128/898 |
| 5,399,163 A | | 3/1995 | Peterson et al. | 604/68 |
| 5,438,984 A | | 8/1995 | Schoendorfer | 128/632 |
| 5,441,490 A | | 8/1995 | Svedman | 604/289 |
| 5,527,288 A | | 6/1996 | Gross et al. | 304/140 |
| 5,533,971 A | | 7/1996 | Phipps | 604/20 |
| 5,540,669 A | | 7/1996 | Sage, Jr. et al. | 604/290 |
| 5,582,586 A | | 12/1996 | Tachibana et al. | 604/20 |
| 5,591,124 A | | 1/1997 | Phipps | 604/20 |
| 5,607,691 A | * | 3/1997 | Hale et al. | 424/449 |
| 5,614,502 A | | 3/1997 | Flotte et al. | 514/34 |
| 5,636,632 A | | 6/1997 | Bommannan et al. | 128/632 |
| 5,658,853 A | | 8/1997 | Kassebaum et al. | 424/402 |
| 5,658,892 A | | 8/1997 | Flotte et al. | 518/44 |
| 5,662,624 A | | 9/1997 | Sundstrom et al. | 604/291 |
| 5,667,491 A | | 9/1997 | Pliquett et al. | 604/50 |
| 5,718,955 A | | 2/1998 | McGuire et al. | 428/35.7 |
| 5,730,714 A | * | 3/1998 | Guy et al. | 604/20 |
| 5,779,698 A | | 7/1998 | Clayman et al. | 606/39 |
| 5,853,383 A | | 12/1998 | Murdock | 604/20 |
| 5,857,992 A | | 1/1999 | Haak et al. | 604/20 |
| 5,885,211 A | | 3/1999 | Eppstein et al. | 600/309 |
| 5,964,726 A | | 10/1999 | Korenstein et al. | 604/20 |
| 5,983,131 A | * | 11/1999 | Weaver et al. | 604/20 |
| 6,050,988 A | | 4/2000 | Zuck | 604/890.1 |
| 6,083,196 A | | 7/2000 | Trautman et al. | 604/46 |
| 6,104,952 A | | 8/2000 | Tu et al. | 604/20 |
| 6,132,755 A | | 10/2000 | Eicher et al. | 424/427 |
| 6,148,232 A | * | 11/2000 | Avrahami | 604/20 |
| 6,149,620 A | * | 11/2000 | Baker et al. | 604/22 |
| 6,175,752 B1 | * | 1/2001 | Say et al. | 600/645 |
| 6,527,716 B1 | | 3/2003 | Eppstein | 600/309 |
| 6,611,706 B1 | * | 8/2003 | Avrahami et al. | 604/20 |
| 6,615,079 B1 | | 9/2003 | Avrahami | |
| 2001/0023330 A1 | | 9/2001 | Palti | 604/20 |

FOREIGN PATENT DOCUMENTS

| | | |
|---|---|---|
| WO | 93/17754 A1 | 9/1993 |
| WO | 94/23777 A1 | 10/1994 |
| WO | 95/30410 A3 | 11/1995 |
| WO | 96/17648 A1 | 11/1995 |
| WO | 96/00110 A1 | 1/1996 |
| WO | 96/37256 A1 | 11/1996 |
| WO | WO 97/04832 | 2/1997 |
| WO | 97/12644 A1 | 4/1997 |
| WO | WO 97/48440 | 12/1997 |
| WO | 97/48441 A1 | 12/1997 |
| WO | 97/48442 A1 | 12/1997 |
| WO | 98/11937 A1 | 3/1998 |
| WO | 98/28037 A1 | 7/1998 |
| WO | 98/28038 A1 | 7/1998 |
| WO | WO 98/29134 | 7/1998 |
| WO | 98/46124 A1 | 10/1998 |
| WO | WO 00/69515 A1 | 11/2000 |
| WO | WO 01/13989 A1 | 3/2001 |

OTHER PUBLICATIONS

Brand et al., An experimental model for interpreting percutaneous penetration of oligonucleotides that incoporates the role of keratinocytes, 1998, The Journal of Investigative Dermatology, vol. 111, pp. 1166–1171.*

Henry et al., Microfabricated microneedles: A novel approach to transdermal drug delivery, 1998, Journal of Pharmaceutical Sciences, vol. 87, pp. 922–925.*

Sun, Y. Skin Absorption Enhancement by Physical Means: Heat, Ultrasound, and Electricity. Transdermal and Topical Drug Delivery Systems. (1997) 327–355.

Buyuktimkin N., Buyuktimkin S. Chemical Means of Transdermal Drug Permeation Enhancement. Transdermal and Topical Drug Delivery Systems. (1997) 357–475.

Sun Y., Liu J.C., Xue H. Important Parameters Affecting Iontophoretic Transdermal Delivery of Insulin. Proceed. Intern. Symp. Control. Rel. Bioact. Mater., 17, Controlled Release Society, Inc. (1990) 202–203.

Roberts M. Lai P., Cross S., Yoshida N. Solute Structure as a Determinant of Iontophoretic Transport. Mechanisms of Transdermal Drug Delivery. (1997) 291–349.

Burdick, K., Electrosurgical Apparatus and Their Application in Dermatology, Charles C. Thomas (1966) pp. 2–60.

Pikal, M., The Role of Electroosmotic flow in transdermal iontophoresis, Advanced Drug Delivery Review, 9(1992) pp. 201–237.

Zakzewski, C., Li, J., Amory, D., Jensen, J., Kalatzis–Manolakis, E., Design and implementation of a constant–current pulsed iontophoretic stimulation device, Captopril, Sigma Chemical Co., St. Louis, Missouri, (1996) pp. 484–488.

Jaw, F., Wang, C., Huang, Y., Portable current stimulator for transdermal iontophoretic drug delivery, Med. Eng. Phys. vol. 17, No. 5, (1995)pp. 385–386.

Park, M.R., Constant current source for iontophoresis, Journal of Neuroscience Methods, 29 (1989) pp. 85–89.

Pollack, S., Electrosurgery, Dermatology, Ed. S.L. Moschella and H.J. Hurley, (W.B. Saunders Company, 1992), pp. 2419–2431.

Sebben, J., Cutaneous Electrosurgery, Year Book Medical Publishers, Inc. 1989, pp. 1–211.

* cited by examiner

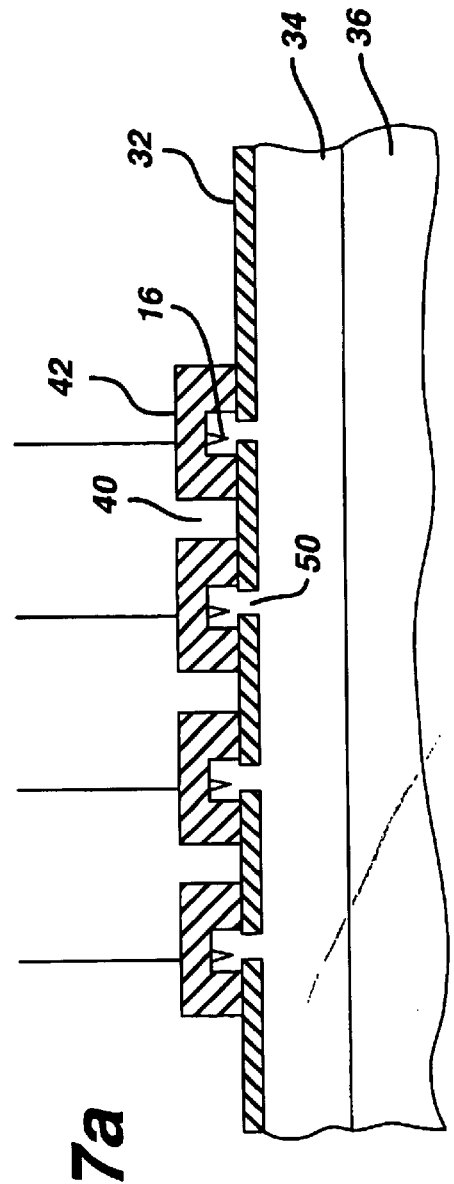
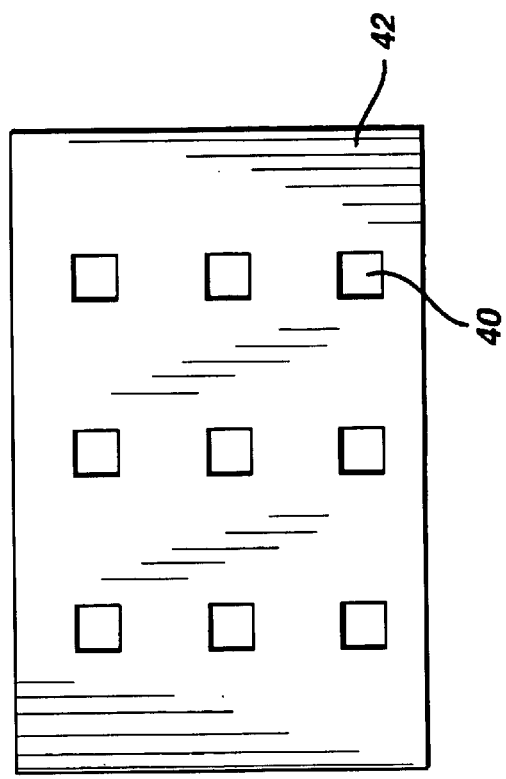
FIG. 7b
FIG. 7a

| Needle electrode |  |
|---|---|
| Wire electrode |  |
| Ball electrode |  |
| Rod electrode (protruding flat tip) |  |
| Plate electrode (Indented flat tip) |  |

Electric insulator

Electrode surface

TISSUE ELECTROPERFORATION FOR ENHANCED DRUG DELIVERY

This patent application claims priority from U.S. Provisional Patent Application No. 60/150,636 filed on Aug. 25, 1999.

FIELD OF THE INVENTION

The present invention relates to methods and devices for the ablation of barrier membranes using electric current in order to both enhance drug delivery for therapeutic purposes and enable sampling of biological substances for diagnostic purposes.

BACKGROUND OF THE INVENTION

Transdermal and topical drug dosage forms have been widely prescribed for decades in the treatment of systemic diseases and local conditions such as those involved with the skin and underlying tissues. These drugs are typically "easy-to-deliver" since they freely permeate through the skin or mucosal membrane with a high potency. Permeation of the drug across the skin or mucosal membrane is a result of the chemical concentration gradient across the membrane. Examples of "easy-to-deliver" drugs include nitroglycerin, scopolamine, nicotine, hydrocortisone, betamethasone, benzocaine, and lidocaine.

Most drugs and biological active ingredients, however, do not easily permeate membranes and, therefore, are categorized as "difficult-to-deliver" drugs. Examples of "difficult-to-deliver" drugs include insulin, vasopressin, erythropoietin, interferons, and growth hormone and its releasing factors. Typically, "difficult-to-deliver" drugs have high hydrophilicity and/or high molecular weight, such as polypeptides, proteins, and polynucleotides (e.g., genes). To increase skin permeation of these drugs, various chemical and physical permeation enhancing methods have been employed. This process, however, is usually only effective for drugs having relatively low molecular weights (e.g., less than approximately 1000 daltons).

Electricity may be employed to facilitate drug transport across the membranes barrier by applying an electric potential gradient across the membrane to facilitate drug transport. There are three such types of electrically facilitated drug transport methods, namely, iontophoresis, electro-osmosis, and electroporation. In iontophoresis, an ionized drug is driven across the membrane by an applied electric potential gradient. In electro-osmosis, a non-ionic or poorly ionized drug is carried by a fluid that is driven across the membrane by an applied electric potential gradient. Electro-osmosis can also be used to extract interstitial fluid out of a body for diagnostic purposes. This process is called "reverse iontophoresis." Electroporation is a process of creating transient microscopic pores on a barrier membrane, by extremely short pulses of high electric voltage and low current. U.S. Pat. Nos. 5,019,034, 5,547,467, 5,667,491, and 5,749,847 describe an "electroporation" method of treating a tissue in order to transiently increase the tissue's permeability to enhance molecular transport either for drug delivery or for sampling of interstitial fluids. All three of these transport methods are described by Sun in "Skin Absorption Enhancement by Physical Means: Heat, Ultrasound, and Electricity," *Transdermal and Topical Drug Delivery Systems*, Interpharm Press, Inc., 1997, pages 327–355.

Although the above electrical methods can provide a powerful driving force for transdermal drug delivery, perforation of barrier membranes (e.g., the stratum corneum of the human skin) is still desirable to further facilitate drug transport. The following references disclose the disruption of the skin barrier membranes with mechanical means, i.e., with either small blades (i.e., microblades) or needles (i.e., microneedles): PCT Patent Applications WO 98/11937 and WO 97/48440; U.S. Pat. Nos. 5,250,023 and 5,843,114; and Henry et al., "Microfabricated Microneedles: A Novel Approach to Transdermal Drug Delivery", S. Henry, D. V. McAllister, M. G. Allen and M. R. Prausnitz, Journal of Pharmaceutical Sciences, Vol. 8, August 1998, pages 922–925.

As an alternative approach, U.S. Pat. No. 5,885,211 describes a method of enhancing the permeability of the skin utilizing microporation by using a hot metal wire heated by electric current. The disclosed "hot-wire" method for stratum corneum ablation comprises an ohmic heating element, namely, a material with high electric resistance that is heated up to very high temperature when an electric current passes through it. This "hot-wire" method described in this patent is similar to electrocautery commonly used in surgery to stop bleeding.

Radio Frequency ("RF") electric current has been used in electrosurgery for various surgical procedures. Electrosurgical machines produce high frequency alternating currents with frequencies of 500 kHz–4000 kHz. These frequencies are part of the low RF range and produced by oscillating circuits. Advantages of electrosurgery, in comparison to other surgical techniques, include simplicity of the technique, high speed, compact equipment, good safety, and applicable to both benign and malignant lesions.

Electrosurgery is different from electrocautery. In eletrocautery, a metal wire that becomes heated as a result of its high resistance to the passage of direct current electricity is used to cut the tissue. The electric current does not pass through the tissue of a patient under treatment, but rather only through the high resistance wire (the ohmic element) in order to heat it up. On the contrary, electrosurgery equipment, capable of producing RF electric current, are used to move or destroy tissue via a "cold" electrode, as described by S. V. Pollack, "Electrosurgery", in Dermatology, Ed. S. L. Moschella and H. J. Hurley, W. B. Saunders Company, 1992, pages 2419–2431). In electrosurgery, the RF current passes through the patient tissue to produce intended heat to cause tissue disruption.

Previously published information regarding use of RF current in electrosurgery field has primarily been focused on the cutting and removing living tissues. The cutting depth is usually well into and often beneath the dermal tissues in dermatological and other surgeries. In contrast, the present invention relates to the novel use of electric current to ablate a barrier membrane (e.g. the stratum corneum of the human skin) to both enhance drug delivery for therapeutic purposes and enable sampling of biological substances for diagnostic purposes.

SUMMARY OF THE INVENTION

In one aspect, the present invention features a method for transporting a molecule through a barrier membrane of at least one layer of cells (e.g., the skin of a mammal such as a human) comprising the steps of: ablating the membrane (e.g., destroying the cells of the membrane) with an electric current from a treatment electrode; and utilizing a driving force to move the molecule through the perforated membrane (e.g., either moved into or out of the mammal through the membrane). Examples of membranes include, but are not limited to, skin, buccal, vaginal, and rectal membranes (e.g., of a human).

The transport processes associated with this invention lend themselves to use with a wide variety of molecules including drugs and molecules of diagnostic interest within the mammal. Molecules (e.g., compounds such as active agents) which may be delivered by the method and/or device of the present invention include, but are not limited to, any material capable of exerting a biological effect on a human body, such as therapeutic drugs, including, but not limited to, organic and macromolecular compounds such as polypeptides, proteins, saccharides, polysaccharides, polynucleotides, and nutrients.

In one embodiment the treatment electrode does not contact the membrane and an electric current forms an electric arc between the treatment electrode and the membrane. In another embodiment, the method further comprises the use of an indifferent electrode, where the electric current passes from the treatment electrode, through the membrane, and to the indifferent electrode. Depending on the mode of an electroperforation application, the two electrodes may or may not have direct contact with the skin.

The electric current may be a direct current, an alternating current, or a mixture thereof. The frequency of the alternating current may be between about 30 Hz to about 10,000 kHz (e.g., between about 60 kHz to about 5 MHz such as between about 100 kHz to about 4 MHz). The voltage of the current, the energy output, the duration of the process, as well as the size, shape and number of the electroperforation electrodes, may vary depending on the size and depth of the ablation required. The voltage may range from about 1 to about 2000 volts (e.g., 5 to 700 volts). The waveform of the electric current may be a damped sine wave, modulated sine wave, pure sine wave, damped square wave, modulated square wave, pure square wave, direct current, or a blend wave thereof.

Examples of driving forces include, but are not limited to: iontophoresis, electro-osmosis, reverse iontophoresis, and electroporation where a delivery electrode and a return electrode are used to transport the molecule through the membrane; phonophoresis where an ultrasonic transducer that converts electric energy into acoustic energy to transport the molecule; pressure gradients where a mechanic apparatus that is capable generating either a positive or negative pressure gradient across the barrier membrane is used, respectively to move molecules into or out of the mammal; heat where the increase in temperature enhances transport of the molecule; and concentration gradients where the higher concentration of the molecule one side of the membrane causes its transport across the membrane.

In one embodiment, the method further comprises the step of piercing the membrane with a member selected from the group consisting of needles or blades. In one embodiment, the method further comprises the step of applying a conductive material to the membrane prior the ablation. Examples of a conductive materials include, but are not limited to, electrolytes, metal particles, or carbon particles. In one embodiment, the method further comprises the step of cooling and/or applying an analgesic to the membrane prior to or during the ablation. In one embodiment, the method further comprises the step of monitoring the electrical resistance (e.g., impedance) of the membrane in order to determine the presence of ablation in the membrane.

In another aspect, the present invention features a device for transporting a molecule through a barrier membrane of a mammal comprising: a housing having a skin contacting surface; a reservoir having an orifice in communication with the skin contacting surface; a current controller for making an electric current capable of ablating the membrane; and a treatment electrode proximate to the skin contacting surface for delivering the current to the membrane where the treatment electrode is in electronic communication with the current controller; wherein upon contacting the skin contacting surface with the membrane, the device is capable of both ablating the membrane with the electric current and transporting the molecule either from the reservoir, through the membrane, and into the mammal or from the mammal, through the membrane, and into the reservoir. The treatment electrode may or may not come into contact with the membrane.

In one embodiment, the device comprises a plurality of treatment electrodes (e.g., between 2 and 200 treatment electrodes, such as between 2 and 50 treatment electrodes, per square centimeter of the electrode surface). In one embodiment, the device comprises an indifferent electrode which is used either as an return electrode when in contact with the membrane to complete the electric circuit in bi-terminal electroperforation, or, when not in contact with the membrane, to help directing the electric energy to the barrier membrane in the mono-terminal mode of electroperforation. See S. V. Pollack, S. V.: "Electrosurgery", in *Dermatology*, Ed. S. L. Moschella and H. J. Hurley, (W.B. Saunders Company, 1992), pages 2419–2431. In one embodiment, the device comprises a sensor for measuring the electrical resistance (e.g., impedance) of the membrane.

In one embodiment, the reservoir comprises an iontophoretic electrode for drug delivery by iontophoresis and/or electro-osmosis, or for interstitial fluid sampling by reverse iontophoresis. In a further embodiment, the reservoir comprises a delivery electrode and a semipermeable membrane (e.g., permeable to the fluid within the reservoir, but not permeable to the molecule being transported through the membrane), wherein the semipermeable membrane separates the delivery electrode and the orifice. In one embodiment, the reservoir further comprises a sensor selected from the group consisting of sensors for measuring the pH, molecule or ion concentration, electric conductivity, amperage, and potential, pressure, color and temperature of the fluid in the reservoir.

In one embodiment, the device further comprises a power supply (e.g., a battery) for providing a source of electric current to the current controller from which the current controller modifies (e.g., via a circuit) the electric parameters of the current (e.g., the voltage, waveform, frequency, and duration) for use in ablating the membrane. In another embodiment, the current controller is capable of being attached to an external power supply.

Other features and advantages of the present invention will be apparent from the brief description of drawings, the detailed description of the invention and from the claims.

BRIEF DESCRIPTION OF THE DRAWINGS

FIG. 7a is a top-view of a schematic representation of an example of an apparatus of the present invention having spacers.

FIG. 7b is a cross-section view of a schematic representation of an example of an apparatus of the present invention having spacers.

DETAILED DESCRIPTION OF THE INVENTION

Figure 1:
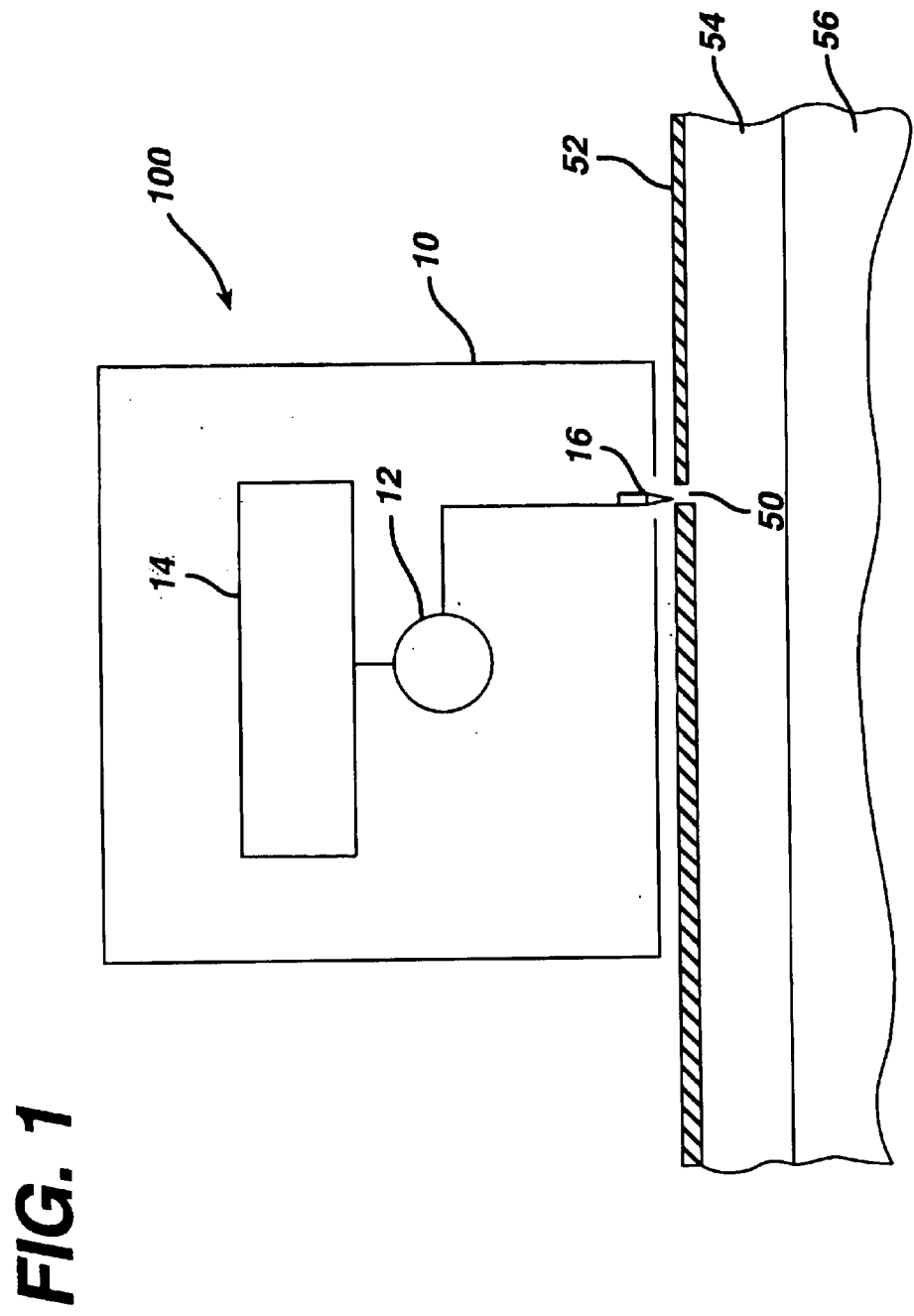
FIG. 1 is a schematic representation of an example of an apparatus of the present invention that can be used for the electroperforation process under a "mono-terminal" condition.

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

In one aspect, the present invention relates to a method whereby it is possible to increase and control the transport of molecules across barrier membranes (e.g., tissues including mammalian skin and mucosal membranes such as rectal, vaginal, and buccal membranes) using an electric current to create openings (e.g., pores) in the membrane as transport pathways for the molecules. This method of ablating the barrier membrane is herein termed as "electroperforation." This ablation J&J-1942 of the membrane (e.g., the destruction of the layer of cells) is a result of the heat generated as the electric current passes through the membrane. As used herein, the term "pore" refers to a disruption of the membrane leading to an increased molecular transport. In this context, a pore is not restricted by its size and shape. For example, it may be a discrete hole having a diameter, for example, of between about 1 µm to about 5 mm (e.g., between about 10µ to about 1 mm), or a line having a length, for example, up to about 10 cm (e.g., up to about 1 cm). An electroperforation process may result in an array of such pores, a grid of the lines, or a mixture thereof.

Because the electroperforation process in the present invention destroys the membrane at the point of application, this transport enhancement method is essentially independent of differences in membrane properties, either between different subjects or on the same subject but on the different anatomic sites. Examples of such differences include the chemical compositions of the membrane (e.g., lipid and ceramide contents), membrane thickness, mechanic properties (e.g., elasticity and toughness), and electric properties (e.g., conductivity), as well as biological characteristics (e.g., numbers and types of sweat glands and hair follicles). These differences are known to have a profound impact on transdermal drug delivery.

For example, stratum cornea with different lipid contents respond differently toward the use of chemical penetration enhancers that primarily affect lipid domain and pathways. Stratum cornea thickness affects most transdermal delivery relying on passive diffusion of drugs. Mechanical properties such as skin elasticity and toughness dictate the outcome of mechanical ablation of stratum corneum utilizing methods described in PCT Patent Applications WO 98/11937 and WO 97/48440, U.S. Pat. Nos. 5,250,023 and 5,843,114, and Henry et al., "Microfabricated Microneedles: A Novel Approach to Transdermal Drug Delivery", S. Henry, D. V. McAllister, M. G. Allen and M. R. Prausnitz, Journal of Pharmaceutical Sciences, Vol. 8, August 1998, pages 922–925. Additionally, sweat glands and hair follicles are known as primary pathways in transdermal drug delivery by iontophoresis. Since transdermal drug delivery through electroperforation with electric current eliminate these variables by creating new openings in the stratum corneum as drug transport pathways, this invention provides a superior method for transdermal and transmucosal drug delivery over methods known in the prior arts.

Furthermore, the pores created by electroporation according the present invention are not transient (in contrast to electroporation), but permanent in a sense these pores will remain open until the new cells re-grow over the opening. This result simplifies the drug delivery process by eliminating the need for constant monitoring the state of the transient microscopic "pores" as in electroporation. Furthermore, in contrast to the electroporation process described in U.S. Pat. No. 5,019,034, it is not necessary to have an electrolyte solution in the electrode chamber for the electroperforation of the present invention to take place. In fact, a small air gap between the stratum corneum and the electrode tip may be used for eletrofulguration, as described below.

Furthermore, unlike the "hot wire" method described in U.S. Pat. No. 5,885,211 which can not be used when the ohmic heating element is immersed in a liquid (e.g., a drug solution), the electroperforation process of the present invention may be conducted in a liquid such as drug solution. It, therefore, is possible to repeat electric current treatment to the skin during a drug delivery process if the pores created previously have closed due to eventual tissue growth or other reasons.

In order to perform the electroporation process, any number of current generating devices may be used.

Figure 8:
FIG. 8 is a cross-section view of a schematic representation of some examples of electroperforation electrode tips that can be used in the apparatus of the present invention.
Figure 8:
Figure 8:
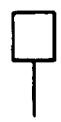
Figure 8:
Figure 8:
Figure 8:
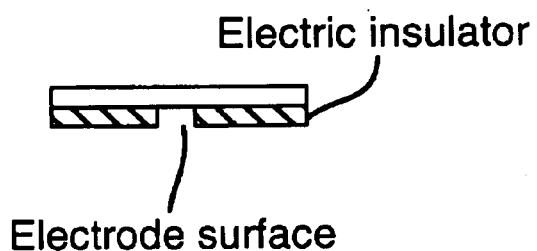

Examples of suitable devices include electrosurgical devices currently on the market (e.g., Bovie® Specialist and Aaron 800™ both by Aaron Medical Industries, St. Petersburg, Fla.; Surgitron FFPF, Ellman International Inc., Hewlett, N.Y.; and Hyfrector 2000, by ConMed Corporation, Englewood, Colo.). It should be noted that the electroperforation apparatus can be fabricated into any shapes, sizes with various physical properties to suite various therapeutic applications. For example, as shown in FIG. 8, it can be made in the shape of a plate, a rod, a thin wire, a sharp needle, a blade, or a ball. The following publications describe the circuits, for generating electric currents for electrosurgery. These circuits can be used in the devices to be used for the electroporation process of the present invention: S. V. Pollack, S. V.: "Electrosurgery", in *Dermatology*, Ed. S. L. Moschella and H. J. Hurley, (W.B. Saunders Company, 1992), pages 2419–2431; K. H. Burdick in *Electrosurgery Apparatus and Their Applications in Dermatology*, Charles C. Thomas Publisher, 1966; J. A. Pearce in *Electrosurgery*, John Wiley & Sons, Inc., 1986; J. A. A. Langtry and A. Carruthers, "True Electrocautery in the Treatment of Syringomas and Other Benign Cutaneous Lesions". J Cutaneous Medicine and Surgery 1997, 2:1:60–63; J. G. Levasseur, J. G. "Dermatologic Electrosurgery in Patients with Implantable Cardioverter-Defibrillators and Pacemakers", Dermatologic Surgery 1998, 24:233–240; J. E. Sebben in *Cutaneous Electrosugery*, Chicago: Year Book Medical Publications, 1989; S. V. Pollack, in *Electrosurgery of the Skin*, New York: Churchhill, Livingston, 1991; R. Usatine, et al. in *Skin Surgery: A Practical Guide*, Mosby, 1998; B. C. Schultz, in *Office Practice of Skin Surgery*, W B Saunders, 1985; C. Lawrence in *An Introduction to Dermatological Surgery*, Blackwell Science, 1996; and S. Burge in *Simple Skin Surgery*, Blackwell Science, 1996. The following patent disclosures describe the circuit designs, electrode designs and application methods for electrosurgery and endoscopic procedures: U.S. Pat. Nos. 5,451,224, 4,231,372, 5,282,799, 5,514,130, 5,785,705, 5,865,788, 5,545,161, 5,542,916, 5,540,681, 5,383,917, 5,125,928, 5,792,138, 4,071,028, 4,674,499, 4,805,616, 5,269,780, 5,693,052, 5,098,430, 4,979,948, 4,532,924, 5,785,705, 5,893,885, 5,906,613, and 5,897,553.

The outcome of an electroperforation process, such as the effects on a biological tissues and pore formation, is dependent upon the selection of the waveform, frequency, amperage, voltage, and the application technique of the electric current. All these criteria depend on circuit and electrode designs. Further, the electric current for electroperforation in the present invention may be applied in a continuous or a discontinuous fashion.

There are five typical waveforms (i.e., electrofulguration, electrodesiccation, electrocoagulation, pure cut electrosection, and blend electosection) used in electrosurgery as summarized in TABLE 1), all of which are also useful for the electroperforation in the present invention.

TABLE 1

| MODE OF APPLICATION (MODALITY) | WAVE FORM | APPLICATION TECHNIQUE AND BIOLOGICAL EFFECT |
| --- | --- | --- |
| Electro-fulguration | Damped sine wave form | No electrode-membrane contact; arc from electrode tip to membrane; Mono-terminal |
| Electro-desiccation | Damped sine wave form | Electrode-membrane contact; Mono-terminal |
| Electro-coagulation | Moderately Damped | Electrode-membrane contact; Bi-terminal |
| Electro-section Pure Cut | Pure sine wave | Electrode-membrane contact; Bi-terminal |
| Electro-section Blend | Modulated sine wave | Electrode-membrane contact; Bi-terminal |

Visual diagrams of these waveforms are depicted on page 22 of Sebben, Cutaneous Electrosurgery (Year Book Medical Publishers, 1989). The waveforms may be generated by a spark gap circuit or an electronic circuit (e.g., a solid state circuit). See Pollack, "Electrosurgery," in Dermatology, eds. Moscella, et al. (W. B. Sanders, 3d. ed. 1992). Other waveforms, such as any symmetric, asymmetric, or irregular waveforms (e.g., square waveform, damped square waveform, combination waveform of various waveforms and frequencies) may also be used for electroperforation.

The terms "mono-terminal" and "bi-terminal" are used herein to describe the method of delivery of the current to the patient. Mono-terminal refers to the use of a treatment electrode without an indifferent electrode. True electrodesiccation and its variant, electrofulguration, are considered mono-terminal procedures. Bi-terminal denotes that both treatment and indifferent electrodes are used, as in electrocoagulation and electrosection. When utilizing a bi-terminal procedure, the treatment and indifferent electrodes can be in a concentric relation to each other, with the treatment electrode in the center and the indifferent electrode positioned concentrically around the treatment electrode. The indifferent electrode may have a much greater membrane contacting surface to help disperse the current. The two electrodes may also be placed apart (e.g., on the same or opposite sides of the membrane).

The measurement of the changes in the electric resistance or impedance of the barrier membrane undergoing the electroperforation process can be used to provide an indication of the occurrence of electroperforation with electric current, thereby providing a basis for selecting the magnitude and duration as well as the waveforms of the electric current. In one embodiment of this invention, the values and changes in values of the electrical impedance between a pair of electrodes, either during or after electric current treatment or treatment series, are monitored to allow a determination of the occurrence and/or extent of electroperforation for any tissue transport situation. More specifically, by monitoring the electrical resistance or impedance between a pair of electrodes, e.g., using a low level alternating current with a frequency between 100 Hz and 10,000 Hz, the mass transport resistance associated with low molecular weight ionic species such as sodium cations and chloride anions, which occur at naturally high concentrations in biological tissues, can be used to indicate the occurrence of electroperforation.

The membrane site undergoing electroperforation may also be pretreated to render it more electrically conductive to facilitate the electroperforation. A topical composition containing conductive materials such as electrolytes or carbon and/or metal powders, in the form of solution, suspension, gel, cream, or lotion, may be applied to the membrane prior to the electroperforation process. The compositions typically contain water, and may also contain organic solvents as vehicles. One example of such a preparation is a solution containing about 0.5–about 5% NaCl, about 70% ethanol and/or isopropyl alcohol and about 29.5%–about 25% water. Alternatively, a conductive coating layer for the tissue, containing a film-forming polymer or gelling agent, may also be used for this purpose. One example of such a coating layer is a thin hydrogel or a hydrocolloidal gel layer containing electrolyte ions One example of such a preparation is a gel containing about 1% hydroxypropyl cellulose, about 0.9% sodium chloride, and about 98.1% distilled water. Suitable gelling agents include, but are not limited to, agar, gelatin, pectins, gums (e.g., alginates, karaya gum, gum arabic, tragacanth gum, carrageenan gum, guar gum, gum ghatti, locust bean gum, tamarind gum and xanthan gum), and hydrophilic cellulose polymers (e.g., hydroxymethylcellulose, hydroxyethylcellulose, hydroxypropylcellulose and carboxymethylcellulose), polyacrylamide, polyethylene oxide, polyethylene glycols, polypropylene glycols, polyvinyl alcohol, polyvinylpyrrolidone, starch, polyacrylic acid, polyacrylates, and derivatives, copolymers, and polymer blends of aforementioned polymers. Other gelling agents are listed in Hand of Water-soluble Gums and Resins, eds. Crawford and Williams, (1980, McGraw-Hill, Inc.).

The tissue site undergoing electroperforation may be cooled to a temperature below ambient temperature prior to and during the electroperforation process in order to minimize potential discomfort and living tissue damage. The cooling process may be accomplished by spraying a cryogenic liquid directly onto the membrane prior to the electroperforation process. Examples of cryogenic liquids include, but are not limited to, fluorinated chlorinated hydrocarbons such as tetrafluoroethane, ethyl chloride and ethyl fluoride, dimethyl ether, propane, isobutane, liquid nitrogen, or other liquefied gases.

The cooling may also be accomplished by contacting the tissue with a heat sink device, which is made of a heat conducting material (e.g., a metal) and contains a cryogenic liquid. As the cryogenic liquid is allowed to evaporate with a proper releasing mechanism (e.g., through a releasing valve), the temperature of the metal is lowered. Alternatively, instead of using a cryogenic liquid above, the heat sink may be cooled from endothermic dissolution process, such as dissolving certain materials (e.g., potassium or sodium nitrate, urea) into water. The advantage of using a heat sink is that no direct contact is necessary between the cryogenic liquid and the tissue, thus avoiding potential side effects of the liquid such as tissue irritation.

An advantage of the electroperforation process is its ability to increase desired material transport across the barrier membrane which otherwise is rather impermeable. Thus, the present invention further pertains to a process of utilizing a driving force to move molecules across the regions of the membrane undergoing, or having undergone, electroperforation with electric current. The driving force to move molecules across the perforated barrier membrane may be electrical in nature, such as iontophoresis, electro-osmosis, reverse iontophoresis, or electroporation. The driving force may also be of acoustic energy in nature, such as in the case when ultrasound (i.e., frequencies above 20 kHz) or an audible sound (i.e., frequencies below 20 kHz) is used to enhance drug delivery (a process called "phonophoresis"). The driving force may also be other physical or chemical force such as provided by a temperature gradient, a pressure gradient, or simply a concentration gradient (e.g., a concentrated form of the material to be transported is held in a reservoir contacting the tissue surface at the site of electroperforation). With respect to the use of a concentration gradient, the driving forces of concentration difference in combination with an externally elevated hydrostatic pressure causes the material to pass through the electroperforation-generated pores into the underlying tissue.

Thus, an electric force, in a form of iontophoresis, electroporation, electro-osmosis, or reverse iontophoresis, can be used as the driving force to transport molecules across the tissue once the pores have been formed through electroperforation. Simultaneously with or subsequent to the completion of electroperforation, an electrical potential of much lower voltage and greater duration for iontophoresis is applied to the electroperforated skin site. Ions present in this low voltage field will migrate toward sources of opposite charge. Thus, if an electrode is present at another distant site, oppositely charged drug ions will migrate through the pores created by electroperforation into the body. Neutral molecules can also be moved by electro-osmosis for transdermal delivery or by reverse iontophoresis for interstitial fluid sampling. A single apparatus in the present invention may have the build-in capability to operate several functions simultaneous or in sequence. Taking gene delivery to dermal tissue as an example, a three-step process may be conducted: (1) using electric current to create pores on stratum corneum by electroperforation, (2) applying iontophoresis to transport the genes across the stratum corneum into living epidermis and dermis tissues, and (3), applying electroporation to increase gene uptake into the epidermis and dermis cells by increasing cell membrane permeability. The U.S. Pat. Nos. 5,019,034, 5,547,467, 5,667,491, and 5,749,847 and PCT Patent Application WO 99/22809 describe the use of electroporation to increase tissue permeability. Iontophoresis and electroporation in the steps (2) and/or (3) may also be replaced by phonophoresis.

The transport processes associated with this invention lend themselves to use with a wide variety of molecules including drugs and molecules of diagnostic interest. Molecules (e.g., active agents) which may be delivered by the method and/or device of the present invention include, but are not limited to, any material capable of exerting a biological effect on a human body, such as therapeutic drugs, including, but not limited to, organic and macromolecular compounds such as polypeptides, proteins, polysaccharides, nucleic acid materials comprising DNA, and nutrients. Examples of polysaccharide, polypeptide and protein active agents include, but are not limited to, heparin and fragmented (low molecular weight) heparin, thyrotropin-releasing hormone (TRH), vasopressin, gonadotropin-releasing hormone (GnRH or LHRH), melanotropin-stimulating hormone (MSH), calcitonin, growth hormone releasing factor (GRF), insulin, erythroietin (EPO), interferon alpha, interferon beta, oxytocin, captopril, bradykinin, atriopeptin, cholecystokinin, endorphins, nerve growth factor, melanocyte inhibitor-I, gastrin antagonist, somatostatin, encephalins, cyclosporin and its derivatives (e.g., biologically active fragments or analogs).

Other examples of active agents include anesthetics, analgesics, drugs for psychiatric disorders, epilepsies, migraine, stopping drug additions and buses; anti-inflammatory agents, drugs to treat hypertension, cardiovascular diseases, gastric acidity and GI ulcers; drugs for hormone replacement therapies and contraceptives; antibiotics and other antimicrobial agents; antineoplastic agents, immunosuppressive agents and immunostimulants; and drugs acting on blood and the blood forming organs including hematopoietic agents and anticoagulants, thrombolytics, and antiplatelet drugs. Other active agents suitable for transdermal delivery to treat allergies are selected from the group consisting of fine particles or extracts from natural substances (e.g., from herbs, grass seeds, pollens, and animal debris). Also, other cationic and anionic active agents, such as those described in M. Roberts, et al., "Solute Structure as a Determinant of Iontophoretic Transport", *Mechanisms of Transdermal Drug Delivery*, R. O. Potts and R. H. Guy, Ed., Marcel Dekker, pages 291–349, 1997, may be delivered with a device utilizing iontophoresis. Active agents that are non-ionized or with a net charge equal to zero may also be delivered with this apparatus by electro-osmosis as described by Pikal in "The role of Electroosmotic Flow in Transdermal Iontophoresis", Advanced Drug Delivery Reviews, pages 210–238, Vol. 9, 1992. Other active agents that may be used are disclosed in Mosby's Complete Drug Reference Physician's GenRx, ed. BeDell (Mosby-Year Book, Inc., $7^{th}$ ed. 1997) and the Physicians Desk Reference (Medical Economics, $52^{nd}$ Ed, 1998).

Similarly, molecules and substances of diagnostic interest, including both naturally occurring substances and therapeutically introduced molecules in interstitial fluid or blood if deeper penetration is desired, can be extracted out of the barrier membrane by elelctro-osmosis (reverse iontophoresis) for subsequent assaying. These molecules and substances include, but are not limited to, natural and therapeutically introduced metabolites, hormones, amino acids, peptides and proteins, polynucleotides, cells, electrolytes, metal ions, suspected drugs of abuse, enzymes, tranquilizers, anesthetics, analgesics, anti-inflammatory agents, immunosuppressants, antimicrobials, muscle relaxants, sedatives, antipsychotic agents, antidepressants, antianxiety agents, small drug molecules, and the like. Non-limiting representative examples of such materials include glucose, cholesterol, high density lipoproteins, low density lipoproteins, triglycerides, diglycerides, monoglycerides, bone alkaline phosphoatase (BAP), prostate-Specific-Antigen (PSA), antigens, lactic acid, pyruvic acid, alcohols, fatty acids, glycols, thyroxine, estrogen, testosterone, progesterone, theobromine, galactose, uric acid, alpha amylase, choline, L-lysine, sodium, potassium, copper, iron, magnesium, calcium, zinc, citrate, morphine, morphine sulfate, heroin, insulin, interferons, erytheopoietin, fentanyl, cisapride, risperidone, infliximab, heparin, steroids, neomycin, nitrofurazone, betamethasone, clonidine, acetic acid, alkaloids, acetaminophen, and amino acids. In one embodiment, more than one substance is sampled at one time.

In one embodiment, the invention includes a continuous monitoring of the levels of glucose or glucose metabolite (e.g., lactic acid) from the body. The method can also be used for measurement of blood substance (glucose) levels in either a semi-continuous or a single measurement method. The method can be practiced by a device that provides electrodes or other means for applying electric current to the tissue at the collection site; one or more collection reservoirs or sampling chambers to receive the substance (glucose); and a substance concentration measurement system. U.S. Pat. Nos. 5,735,273, 5,827,183, 5,771,890 describe the method of reverse iontophoresis for non-invasive interstitial fluid sampling for diagnostic purpose.

Interstitial fluid may also be extracted from the opening(s) created by electroperforation on the barrier membrane using one of the following methods: mechanical suction device with a structure similar to a syringe; a pre-manufactured vacuum chamber with the working mechanism similar to the Vacumtainer® (Becton, Dickinson and Company, Franklin Lakes, N.J.); placing on the opening(s) a capillary tube or an absorbent material (e.g., gauze or non-woven pad, sponge, hydrophilic polymers of porous structure); or combining aforementioned methods. For example, interstitial fluid can be extracted out of the pore(s) following electroperforation using either a vacuum or an osmotic pressure by contacting the perforated skin with a hygroscopic material such as glycerin, urea, polyvinylidone polymer either alone or as a concentrate aqueous solution. The glucose and other biological substances of interest in the extracted interstitial fluid can be analyzed by the methods described in D. Buerk, Biosensors—Theory and Applications (Technomic Publishing Company, Inc., 1993), and in the U.S. Pat. Nos 5,789,255, 5,453,360, 5,563,031, 5,304,468, 5,563042, and 5,843692.

After the interstitial fluid is driven out of the barrier membrane (e.g., the skin) through the opening(s) created by the electroperforation process by one or more aforementioned driving forces, analysis of certain biological substances in the interstitial fluid can be performed with an analytical method such as a sensor based on enzymatic reaction, antibody interaction, ion-selective electrode, oxidation-reduction electrode; infrared (IR), ultraviolet (UV) spectrophotometry, or colorimetry.

The invention features an apparatus for performing the electroperforation methods of the present invention. One embodiment of an apparatus for producing the pores in a barrier membrane via electroperforation is represented schematically in FIG. 1. In FIG. 1, the apparatus, represented generally as 100, comprises a housing 10, a current generator 14, a current controller 12, and a treatment electrode 16 for electroperforation in mono-terminal operation. The housing 10 may be fabricated from a variety of materials such as metal or plastics commonly used to fabricate the housings of medical devices. The current generator 14 may either comprise a power supply (e.g., a battery such as single use batteries made of alkaline, silver, lithium or high capacity batteries used in implantable electromedical devices; rechargeble Ni—Cd or other types of batteries) or can be connected to a power supply (e.g., plugged into a wall electrical outlet). The current controller 12 comprises a circuit that establishes and/or modifies the parameters of the electric current (e.g., the waveform, polarity, voltage, amperage, and duration) from the current generator 14.

In operation, the treatment electrode 16 is placed in contact with, or at a small distance from, the surface of the stratum corneum 52. The current generator 14 and the current controller 12, in communication with the treatment electrode 16, provides an electric current of a specific wave form, frequency, voltage, amperage, and duration to the treatment electrode 16. The electric current passes from treatment electrode 16 to the stratum corneum 52. As a result of the passing electric current, the stratum corneum 52, at the application site, is destroyed and a small pore 50 is formed. In one embodiment, there is no damage, or only minimal damage inflicted to the living tissues epidermis 54 and dermis 56.

The waveform, frequency, voltage, amperage, and duration of the electric current are controlled by current controller 12. The electric current may be applied for only a short period, such as less than 5 seconds (e.g., less than 1 second or less than 100 milliseconds), to accomplish a desired effect of electroperforation. The electric current may be also applied in a series of short pulses until the electroperforation is satisfactory. At that point, the electroperforation process is completed, and the barrier membrane of the tissue is perforated (e.g., becoming permeable to the molecules to be delivered during a subsequent delivery process).

The resulting pore 50 serves as the transport pathway for molecules of interest, such as a pharmaceutical for therapeutic treatment or interstitial fluid for diagnostic sampling. In the case of pore formation for sampling interstitial fluid, there can be a slightly more damage intentionally done by electroperforation to the underlying living tissues so that more interstitial fluid or even blood can be collected through the pore 50.

In one embodiment, a second electrode (not shown), or the same treatment electrode 16, can be used to monitor electrical resistance or impedance through stratum corneum 52. U.S. Pat. No. 5,738,107 describes a method for impedance measurement and an electric circuit that can be used in this invention. Other impedance measurement circuits commonly used in biomedical devices are also suitable for this purpose. The electrode for electric resistance/impedance measurement may be operatively connected to the current controller 12 and serve as a means for detecting the electroperforation effect occurring during the electric current application. Thus, it serves to inform the current controller 12 of the time point at which the electroperforation process should be terminated and/or reinstated. Since the stratum corneum contributes to almost all the electric resistance of the skin, prompt detection of the elimination of the electric resistance by electroperforation by the treatment electrode 16 or the additional electric resistance-detecting electrode enables the current controller 14 to shut off the electric current in time to avoid any undesirable tissue damage.

Figure 2A:
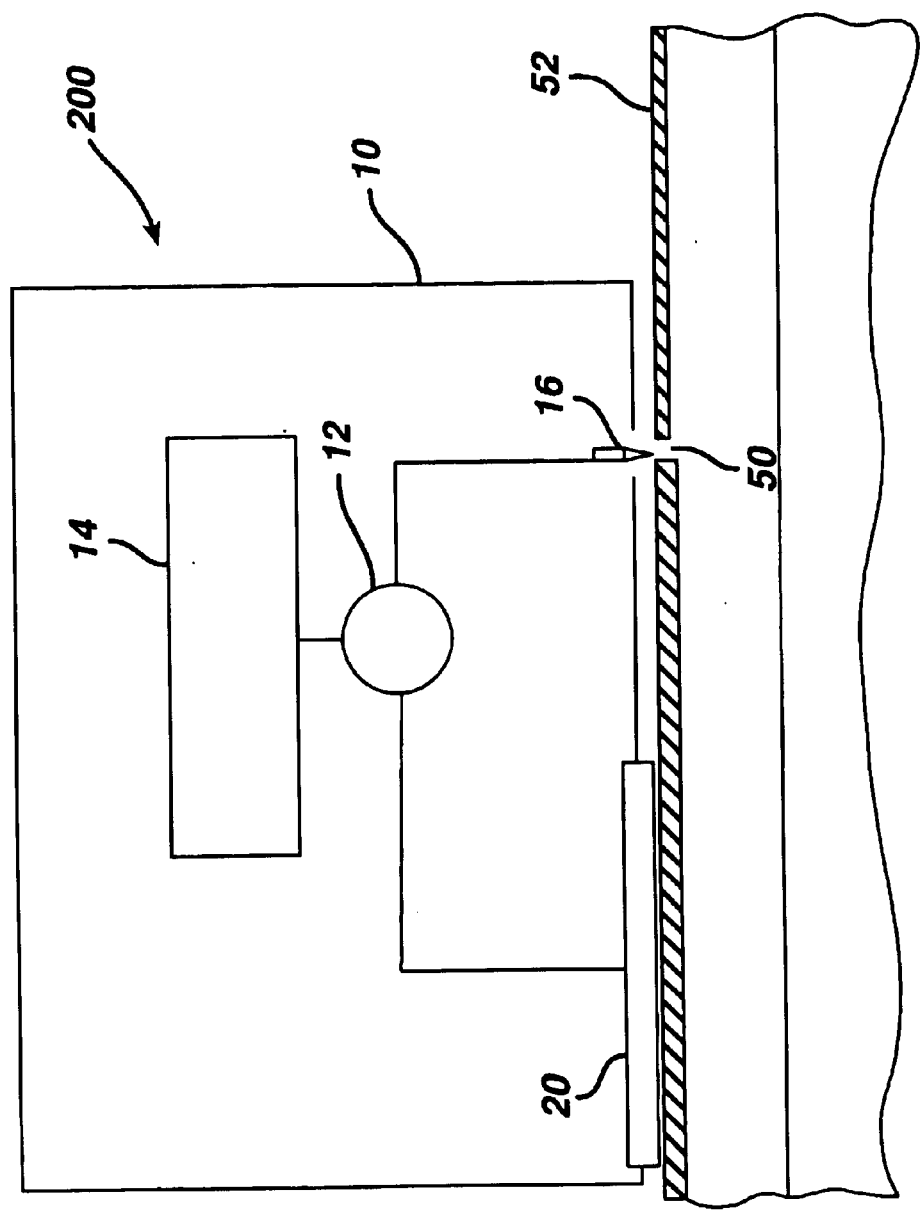
FIG. 2a is a schematic representation of an example of an apparatus of the present invention that can be used for the electroperforation process under a "bi-terminal" condition, using one small treatment electrode and one large indifferent electrode.

Another embodiment of an electroperforation apparatus of the present invention, is represented schematically in FIG. 2a. In FIG. 2a, the apparatus, represented generally as 200, comprises a housing 10, an electric current generator 14, an electric current controller 12, a treatment electrode 16 for electroperforation, and an indifferent electrode 20 (which may also be called "return electrode" or a "disperse electrode"). Apparatus 200, thus, is in bi-terminal operation. The apparatus operates much like that of the previous embodiment in FIG. 1, except that instead of being monoterminal, which is suitable for electroperforation by electrofulguration and electrodesiccation, the apparatus 200 works in bi-terminal operation, which is suitable for electroperforation by electrocoagulation and electrosection.

In operation, the treatment electrode 16 is placed in contact with, or at a small distance from, the surface of the stratum corneum 52. The indifferent electrode 20 is placed in contact with the surface of the stratum corneum 52. The current generator 14 and the current controller 12, in communication with the treatment electrode 16 and indifferent electrode 20, provide an electric current of a specific wave form, frequency, voltage, amperage, and duration to the treatment electrode 16. The electric current passes from treatment electrode 16, through the stratum corneum 52, and into the indifferent electrode 20. As a result of the passing electric current, the stratum corneum 52 at the application site is destroyed and a small pore 50 is formed.

Figure 2B:
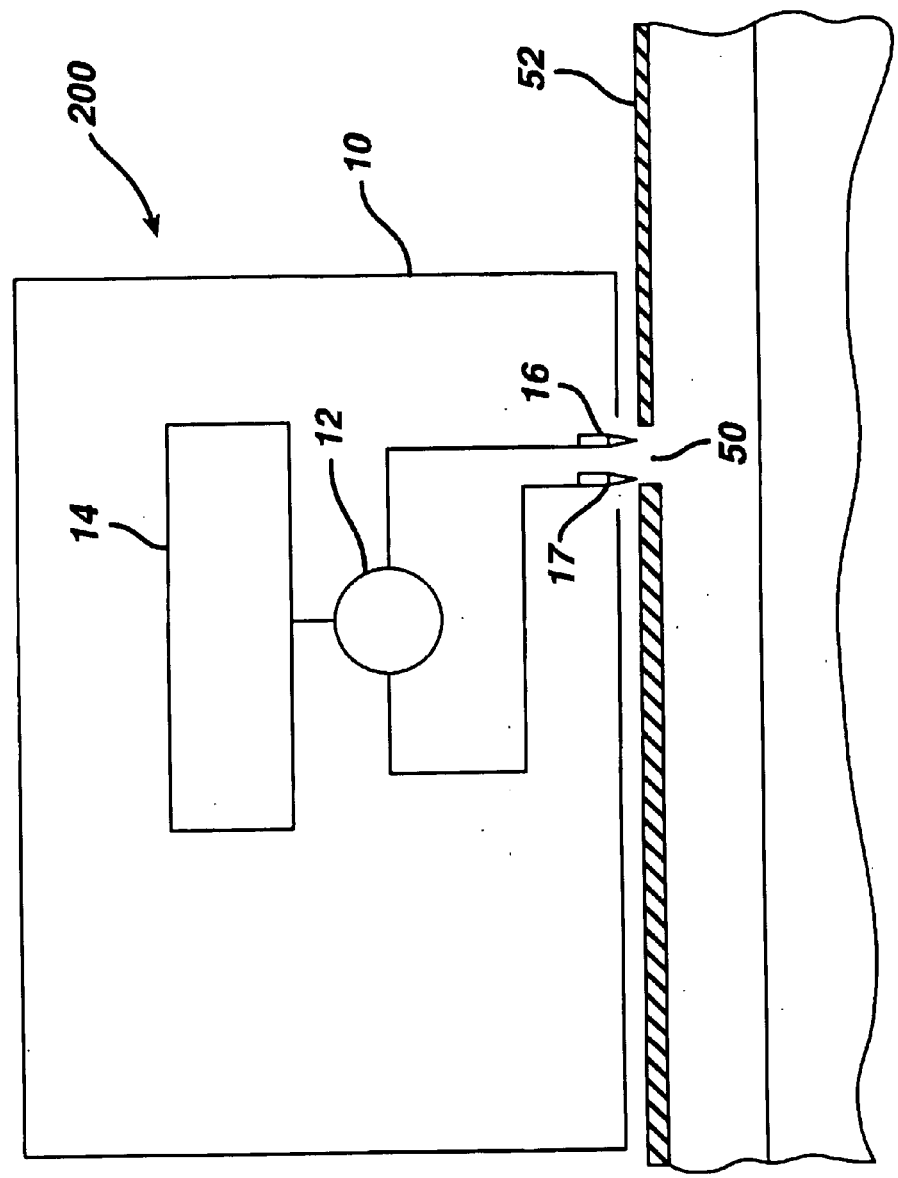
FIG. 2b is a schematic representation of an example of an apparatus of the present invention that can be used for the electroperforation process under a "bi-terminal" condition, using two small, closely positioned electrodes parallel to the barrier membrane.

Another embodiment of an electroperforation apparatus of the present invention is represented schematically in FIG. 2b. It is a bi-terminal apparatus with two electrodes 16 and 17, that are located very close to, but separated from, each other. Either electrode can serve as the indifferent electrode for the other. The primary effect on the membrane during electroperforation is limited to the area immediately between the electrodes 16 and 17, thus confining the tissue action to a very limited area and not incorporating the person under treatment into the general circuit, and minimizing any potential side effects.

Figure 2C:
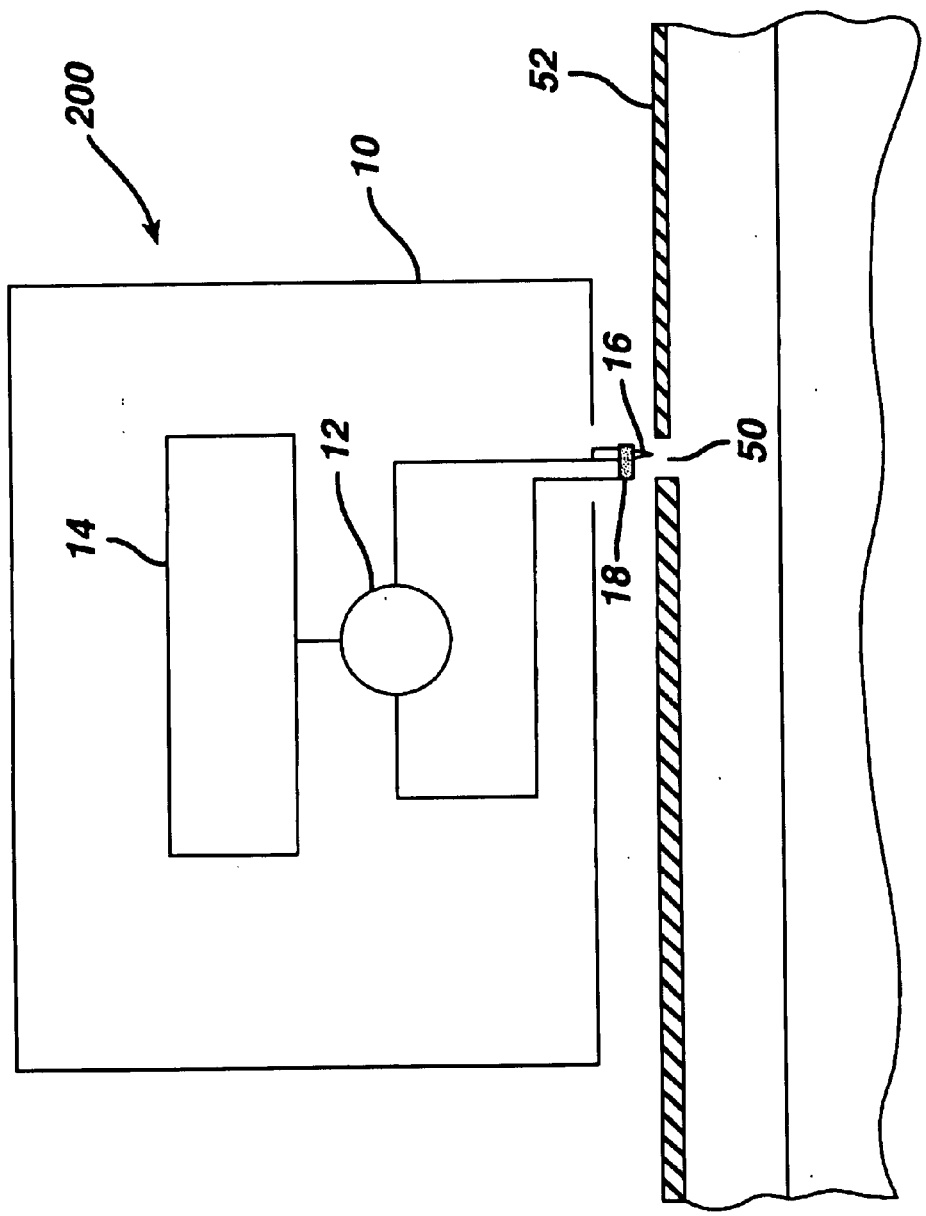
FIG. 2c is a schematic representation of an example of an apparatus of the present invention that can be used for the electroperforation process under a "bi-terminal" condition, using two closely positioned electrodes. The small treatment electrode is located closer to the membrane.

Another embodiment of an electroperforation apparatus of the present invention is represented schematically in FIG. 2c. Similar to the apparatus shown in FIG. 2b, it is also a bi-terminal apparatus with two electrodes 16 and 18. The two electrodes share the same supporting structure but are electrically insulated from each other. The treatment electrode 16 is located closer to the barrier membrane 52 than the indifferent electrode 18. This apparatus is suitable for electroperforation conducted with the electrodes immersed in an electrically conductive solution (e.g., electrolyte solution or a solution containing an ionized drug). The electric current passes from treatment electrode 16, through the barrier membrane stratum corneum, and returns to the indifferent electrode 18. As a result of the passing electric current, the stratum corneum 52 at the application site is destroyed and a small pore 50 is formed.

These apparatuses can be used to pre-treat a membrane by forming pores on the stratum corneum. Subsequent drug application to the pretreated membrane site can be any form of a pharmaceutical preparation, including but not limiting to, a solution, cream, lotion, ointment, gel, spray, aerosol, powder, hydrogel, and a transdermal device in which the pharmaceutical is driven into the skin by a driving force including, but not limiting to, a concentration gradient, pressure gradient, electric force, and ultrasonic energy. For diagnostic purposes, interstitial fluid can be collected from the mammal through the pores using means comprising negative pressure (e.g., a vacuum), electric force (e.g., reverse-iontophoresis), and ultrasound.

Since the subsequent transdermal pharmaceutical delivery method, or interstitial fluid sampling, can be accomplished using, electrical means (e.g., iontophoresis, electro-osmosis, reverse iontophoresis, and electroporation), it is possible to incorporate the components for these delivery devices into the electroperforation apparatus.

Figure 3:
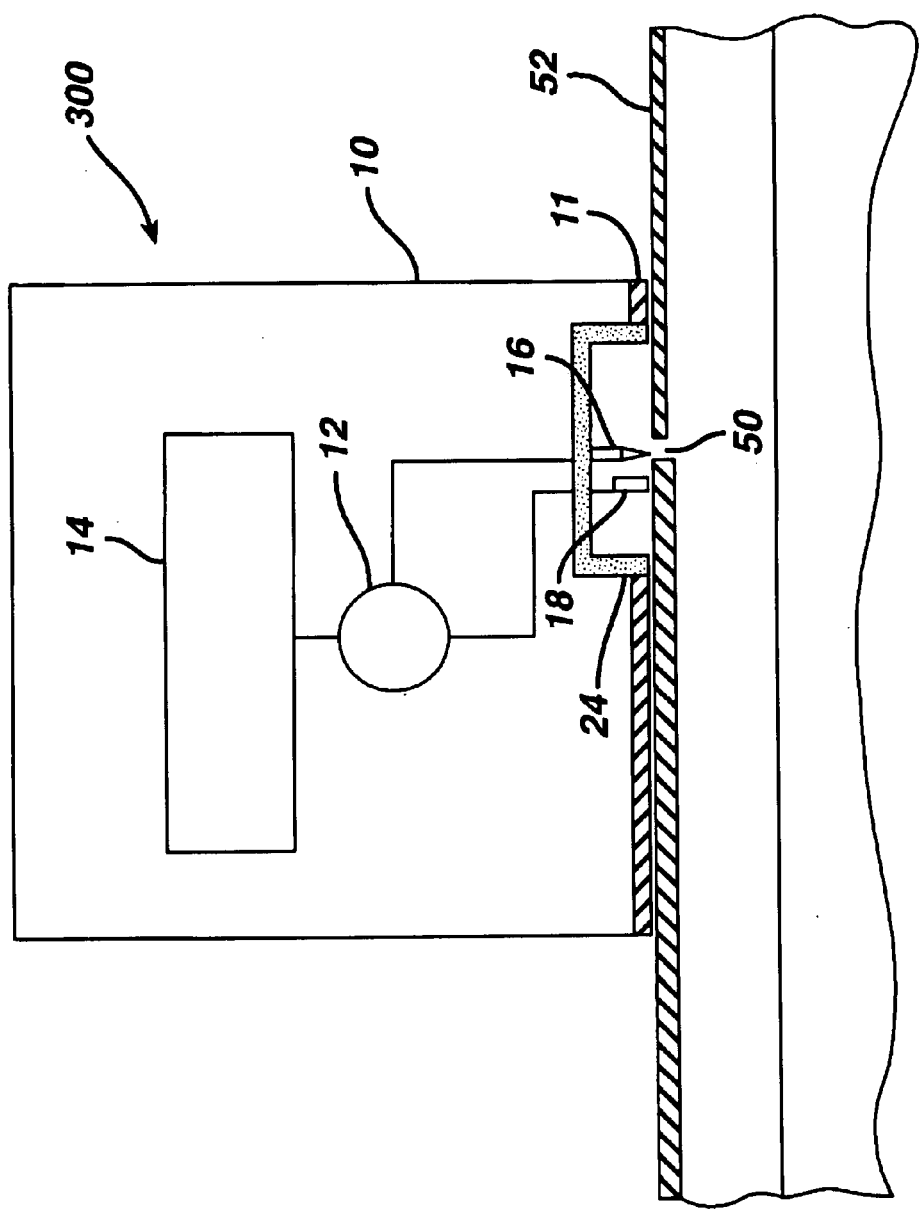
FIG. 3 is a schematic representation of an example of an apparatus of the present invention that can be used both for the electroperforation process and for the transportation of a molecule through the perforated barrier.

Thus, another embodiment of a drug delivery/diagnostic apparatus of the present invention, is represented schematically in FIG. 3. In FIG. 3, the apparatus, represented generally as 300, comprises a housing 10, an electric current generator 14, an electric current controller 12, a treatment electrode 16 for electroperforation in mono-terminal operation, and a sensor electrode 18 for detecting the change in electric resistance across the stratum corneum 52 (e.g., a decrease increase following electroperforation). Depending on the impedance signal obtained by the sensor 18, the electroperforation process can be terminated after the opening 50 is successfully created and the impedance drops, or repeated until desirable results are obtained.

In a one embodiment, apparatus 300 may be used as a minimally invasive means for collecting interstitial fluids for diagnostic purposes. After the electroperforation process is finished, and the interstitial fluids can be transported out of the tissue into the chamber 24 by negative pressure (e.g., a vacuum or osmotic pressure) or ultrasound (devices for generating vacuum, osmotic pressure, or ultrasound not shown). To create an osmotic pressure to extract the interstitial fluid, a concentration amount of a solute species (e.g., highly water soluble salts, carbon hydrates including cellulose polymers and various sugars, urea, solvents such as glycols, polyglycols and glycerol) may be placed in the chamber 24. The interstitial fluid can then be used in a variety of diagnostic procedures.

In another embodiment, the chamber 24 can be used as a drug reservoir for drug delivery into the skin through the pore 50. A drug containing formulation (e.g., as a solution, gel, or any other pharmaceutically acceptable form) can be placed in the chamber 24 for drug delivery purpose.

Figure 4:
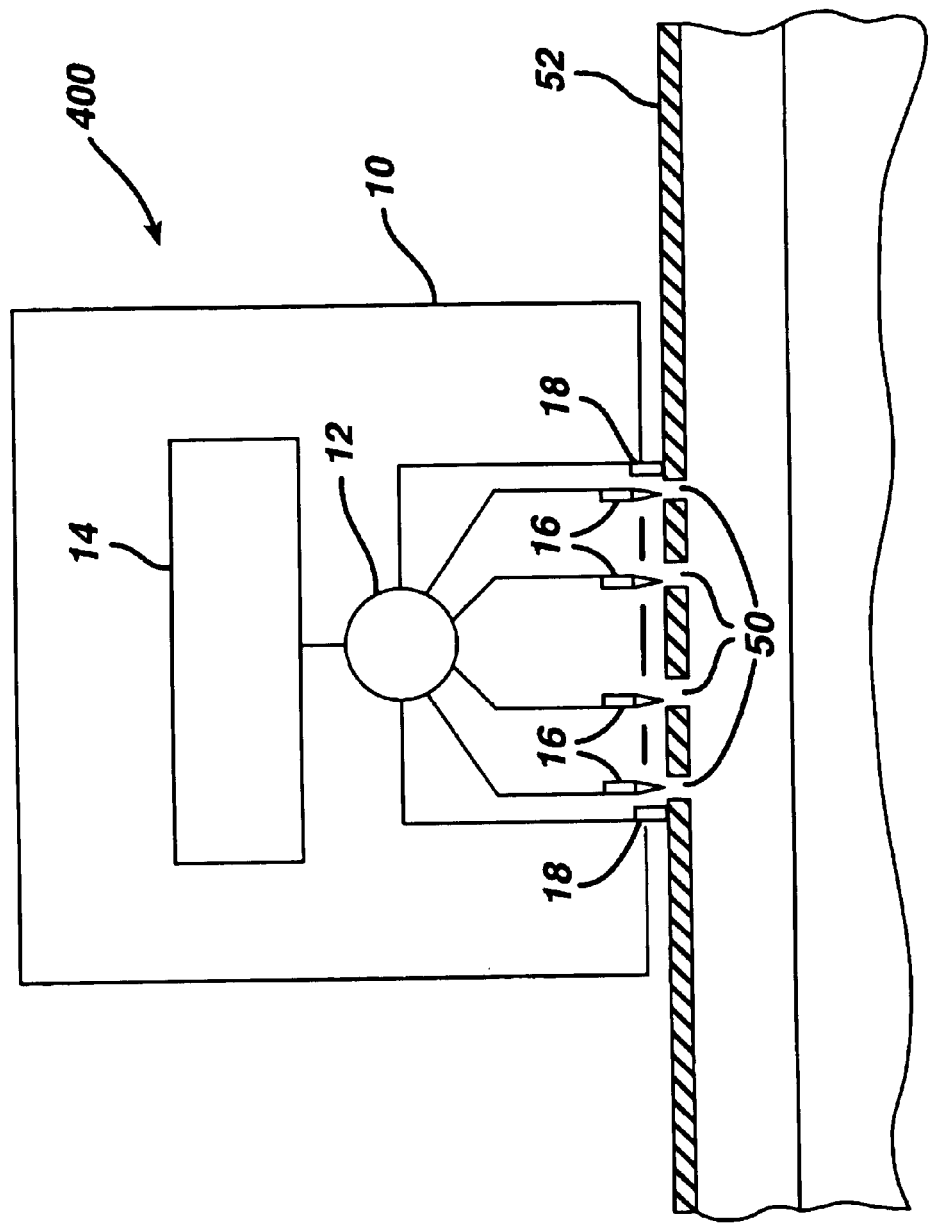
FIG. 4 is a schematic representation of an example of an apparatus of the present invention with four electroperforation electrodes that can be used for the electroperforation process under a "mono-terminal" condition.

Apparatus 300 also comprises an adhesive layer 11 for affixing the device to the barrier membrane. Suitable adhesive materials include those commonly used with medical devices and transdermal patches. The adhesive may be a polymeric, pressure sensitive and nonconductive and remains adherent even after prolonged exposure to water. Typically, the adhesive has a broad working temperature range. Suitable adhesive materials include, but are not limited to, silicones, polyisobutylenes and derivatives thereof, acrylics, natural rubbers, and combinations thereof. Suitable silicone adhesives include, but are not limited to, Dow Corning 355 available from Dow Corning of Midland, Mich.; Dow Corning®X7-2920; Dow Corning®X7-2960; GE 6574 available from General Electric Company of Waterford, N.Y.; and silicone pressure sensitive adhesives, such as those disclosed in U.S. Pat. Nos. 2,857,356, 4,039,707, 4,655,767, 4,898,920, 4,925,671, 5,147,916, 5,162,410, and 5,232,702. Suitable acrylic adhesives include, but are not limited to, vinyl acetate-acrylate multipolymers, including, such as Gelva® 7371, available from Monsanto Company of St. Louis, Mo.; Gelva® 7881; Gelva® 2943; I-780 medical grade adhesive available from Avery Dennison of Painesville, OH; and acrylic pressure sensitive adhesives, such as those disclosed in U.S. Pat. Nos. 4,994,267, 5,186,938, 5,573,778, 5,252,334, and 5,780,050. Alternative affixing methods, such as an elastic or Velcro® strap may also be used. Another embodiment of an apparatus of the present invention, represented generally as 400 having housing 10, contains multiple treatment electrodes 16 for electroperforation as shown in FIG. 4. Such an array of electroperforation electrodes allows a large area of skin 52 to be perforated with multiple pores 50 in a timely manner by the electroperforation apparatus 400. The treatment electrodes 16 may operate either simultaneously or in sequence, as controlled by the current generator 14 and the electric current controller 12. Apparatus 400 also comprises multiple sensor electrodes 18.

Since the subsequent transdermal pharmaceutical delivery method, or interstitial fluid sampling, can be accomplished using, electrical means (e.g., iontophoresis, electro-osmosis, reverse iontophoresis, and electroporation), it is possible to incorporate the components for these delivery devices into the electroperforation apparatus.

Figure 5:
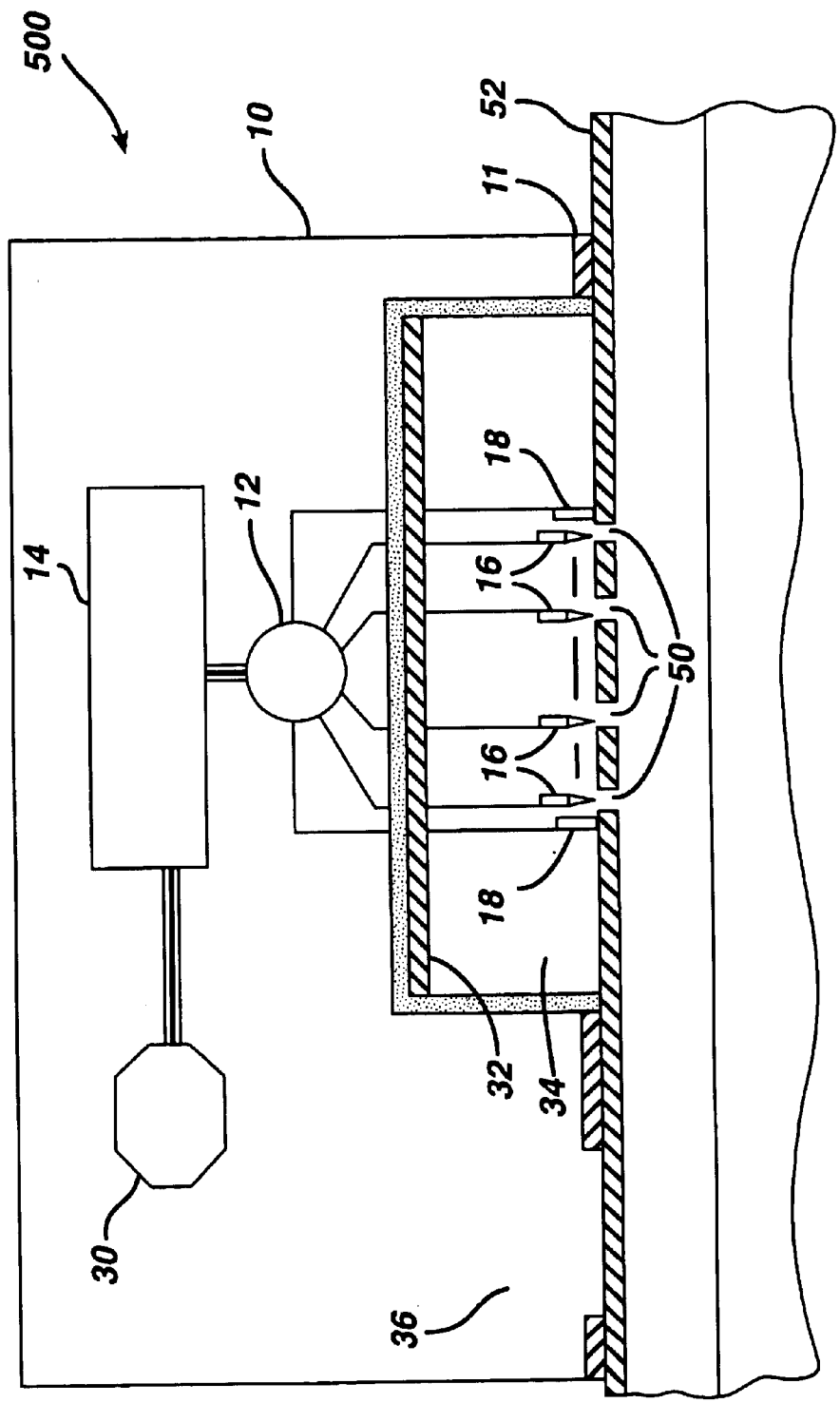
FIG. 5 is a schematic representation of an example of an apparatus that combines an electroperforation unit with an iontophoresis unit. The electroperforation unit has four electroperforation electrodes that can be used for the electroperforation process under a "mono-terminal" condition. The iontophoresis unit is used for the transportation of a molecule through the perforated barrier.

Thus, another embodiment of the apparatus of the present invention, represented generally as 500 in FIG. 5, a transdermal iontophoresis device is incorporated into the electroperforation apparatus. The combination apparatus 500, capable of providing both electroperforation and iontophoresis, comprises a housing 10, adhesive layer 11, an electric current generator 14, an electric current controller 12, treatment electrodes 16 for electroperforation, sensor electrodes 18 for skin resistance detection, a chamber 34 as a drug/interstitial fluid reservoir, a delivery electrode 32 as a conductive electrode for iontophoretic drug delivery, a return electrode 36 to complete the circuit with iontophoretic electrode 32 for iontophoresis operation, and an iontophoresis control unit 30, in communication with the current generator 14, the conductive electrode 32 for iontophoresis, and the return electrode 36.

The iontophoretic drug delivery may be conducted following, or simultaneously with, the electroperforation process. U.S. Pat. Nos. 4,301,794, 4,406,658, 4,340,047, 4,927,408, 5,042,975, and 5,224,927 describe the process of iontophoretic delivery of a substance across tissue that can be used in the present invention.

For delivering a drug through pores 50 in membrane 54, a drug solution may be present or absent during the electroperforation process. In the latter case, the drug solution may be subsequently placed into the chamber 34 (e.g., either through a septum with a syringe or through a port on the wall of the chamber 34 from a breakable capsule (neither shown)) after the electroperforation process is completed.

There may be an optional semipermeable membrane to separate the chamber 34 horizontally into two sub-chambers (not shown). The upper sub-chamber thus created serves as the iontophoresis electrode chamber (containing delivery electrode 32) and the lower sub-chamber serves as the drug reservoir that is in communication with the membrane surface. The semipermeable membrane has pores smaller than the drug molecules being delivered so that the drug molecules can not pass through the semipermeable membrane from the drug reservoir into the iontophoresis electrode chamber (e.g., to be deactivated by the delivery electrode 32).

The combination apparatus 500 may also contain sensors (e.g., sensors for measuring the pH, molecule or ion concentration, electric conductivity, amperage, and potential, pressure, color and temperature of the fluid in chamber 34 (not shown)) to assist in achieving optimal iontophoresis operation. The iontophoresis operation may also use a reverse polarity mode, such as described in U.S. Pat. Nos. 4,406,658, 4,301,794, 4,340,047, and 5,224,927.

Figure 6:
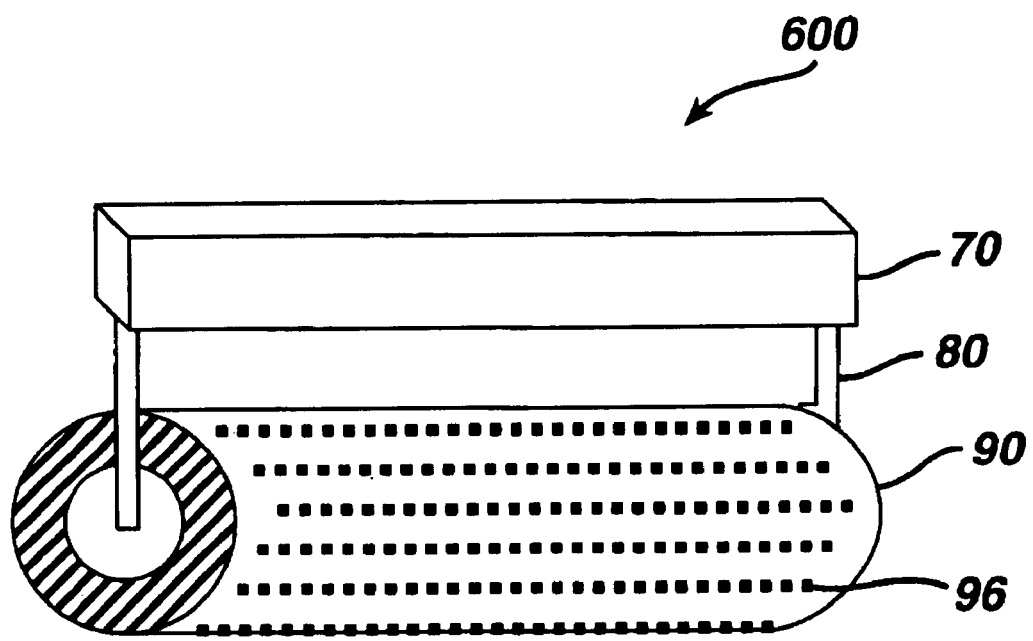
FIG. 6 is a schematic representation of an example of an apparatus of the present invention with a "roller-like" shape.

In yet another embodiment of the present invention, the electroperforation apparatus may be constructed in a form of a "roller-like" device, represented generally as apparatus 600 in FIG. 6. The handle 70 of the roller-like electroperforation apparatus 600 comprises an electric current controller and an electric current generator. The arms 80 are built comprise the connecting wires allowing electric communication between the current controller and current generator in the handle 70 and the electrode array 96 on the roller 90. The body of the roller 90 may contain both an array of treatment electrodes for electroperforation and an array of sensor electrodes for skin resistance detection. It may also contain an iontophoresis unit, as described above.

The "roller-like" electroperforation apparatus 600 is used to create pores on the barrier membrane of a patient. When the apparatus rolls over a skin area, the electroperforation process occurs as the roller surface comes in contact with the membrane, resulting in the formation of numerous pores at pre-determined intervals for a subsequent drug application. The advantages of such an apparatus include an easy and rapid operation over a large membrane area with complex contours.

Alternatively, an electroperforation device in FIG. 6 may be fabricated into a "stamp-like" device where the roller is replaced with a flat or nearly flat surface on which to electrodes are located. In operation, this "stamp-like" electroperforation device can be used to electroperforate the membrane by pressing the surface against the membrane.

In yet another embodiment of the electroperforation apparatus of the present invention, the treatment electrodes 16 may be placed within a spacers 42 as shown in FIG. 7a and 7b. The function of spacers 42 is two fold: (a) separating the treatment electrodes 16 from each other at a predetermined distance and (b) providing a precise distance between the tips of the treatment electrodes 16 and the barrier membrane (e.g., the stratum corneum) 32 to be electroperforated. For example, when electrofulguration or electrodesiccation is the mode of action for an electroperforation process, there should be no direct contact between the treatment electrode 16 and the stratum corneum 32, but rather only a predetermined small gap as controlled by the spacers 42. With other modes of action, such as electrocoagulation and electrosection, the treatment electrode 16 should contact the tissue. In these cases, the spacers 42 prevent undesirable damages to the deeper tissues 34 and 36 other than stratum corneum 32. The open areas 40 provide the liquid pathways for a drug solution to reach the stratum corneum openings 50 from the drug reservoir.

It should be noted that the relative ratio of the open areas 40 to the areas occupied by the spacers 42 and electrodes 16 will vary depending on a particular need. The shapes of the electrodes 16, spacers 42 and the openings 40 may also vary significantly. For example, the tip or the working area of the electrode 16 may be sharply pointed, dull pointed, rounded, blade-like, symmetric or asymmetric, flat, irregularly shaped, with smooth or rough surface. The material used for the electrode 16 may be pure metal, metal alloy, carbon, ceramic, or other any other conductive materials such as conductive composites (e.g., metal-polymer, carbon-polymer, metal-glass; and metal-ceramic) suitable for making the electrodes.

In another embodiment of the invention, the treatment electrode may be made of a consumable material, which is either burned out or melted away during the electroperforation process. For example, when current passes through a thin carbon rod or a carbon fiber to the barrier membrane during the electroperforation process, the heat generated burns out the carbon electrode, thus automatically cutting off the current. This can act as a safety measure to prevent any excess burning which could result from potential malfunction of the current controller. The use of such a consumable electrode to self-terminate the current can also serve as a means to control the duration of electroperforation. Other consumable electrode materials include low melting point metal alloys and metal-polymer composites.

In another embodiment of the invention, the electroperforation electrodes are fabricated as needles or blades. In operation, stratum corneum is first treated by electroperforation. Then the sharp electrodes can be pressed against the electroperforated stratum corneum to further disrupt it. In this case, because it is not necessary to completely perforate the stratum corneum with electric current, a much lower energy power can be used to denature the barrier membrane to make it easier to be penetrated by the needle or blade.

In another embodiment of the invention, the electroperforation process can be conducted while the electrodes are immersed in the drug solution, so that the drug delivery process starts immediately following electroperforation. The electroperforation process can be repeated when necessary (e.g., as indicated by the sensors discussed above).

In another embodiment of the invention, the electroperforation process may be conducted simultaneously with all the treatment electrodes (e.g., the electrodes in the electrode array shown in FIG. 7a and 7b. Alternatively, the electroperforation process may be conducted using only one or a few of electrodes at a given time, and then proceeding stepwise with the other electrodes (e.g., in a fashion resembling a "scanning" action). The mode of turning select electrodes on or off may be controlled by the current controller (e.g., current controller 12 in FIGS. 1–5). The advantage of the "scanning" mode of action is the minimal amount of electric energy required, thus minimizing any potential side effects.

In another embodiment of the invention, a further step is used to retard the closure of the pores (e.g., by keeping the pores occluded for drug delivery or interstitial fluid sampling). In one embodiment, the pores are kept in an aqueous solution that may also contain the drug to the delivered and/or contain compounds that retard epidermal cell differentiation or the tissue growth leading to the closure of the pores. Examples of such compounds include, but are not limited to, saccharides, polysaccharides, cyclodextrins, heparin and fragmented (low molecular weight) heparin derivatives.

To evaluate the feasibility of using electroperforation as a permeability enhancing method to increase transport across a barrier membrane such as the skin, several electroperforation experiments were conducted to examine molecular transport of drugs and water through pig skin in vivo.

EXAMPLE 1

Increase in Transepidermal Water Loss (TEWL) After Electroperforation in Piqs

To evaluate the pore transport pathway created through the stratum corneum of the skin by electroperforation, an in vivo experiment was conducted on the back skin of Yorkshire pigs (female, ~12 kg) using an electrosurgery apparatus (Surgitron™, Ellman International, Inc., Hewlett, N.Y.). The pigs were immobilized with appropriate anesthetics and analgesics. Electrofulguration current was used with a fine wire electrode (0.26 mm in diameter) and power output setting at between scale 3 to 10. A small pore was created on the surface of the skin by carefully moving the electrode towards the skin until the tip of the electrode almost touched the skin. The electrode was quickly moved away from the skin as soon as an electric arc appeared in the gap between the electrode tip and the skin surface.

Figure 9A:
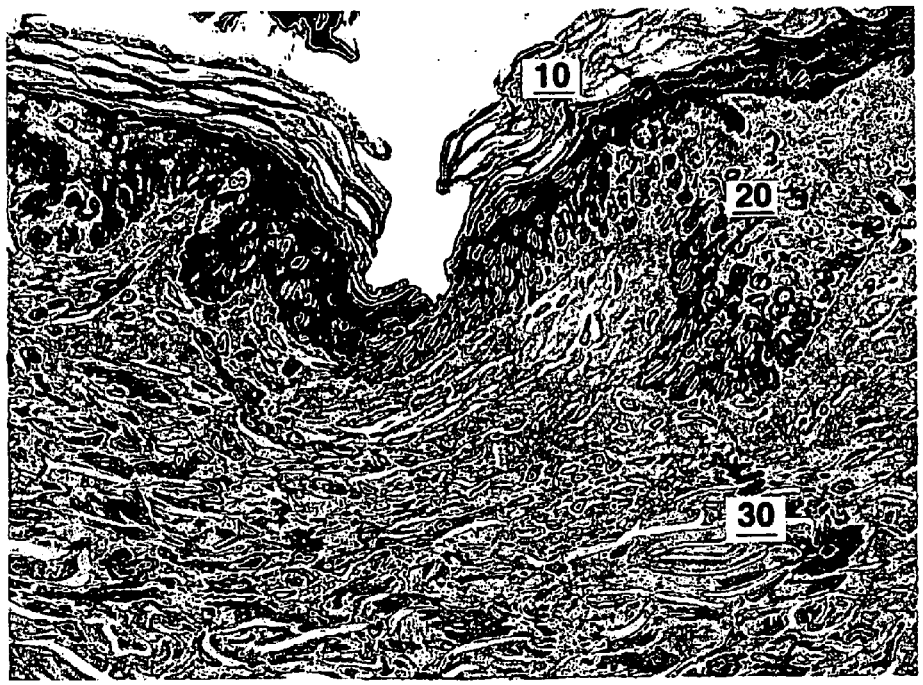
FIG. 9 (a and b) shows typical microscopic biopsy results (magnification=220×) of pig-skin treated with electroperforation.
Figure 9B:
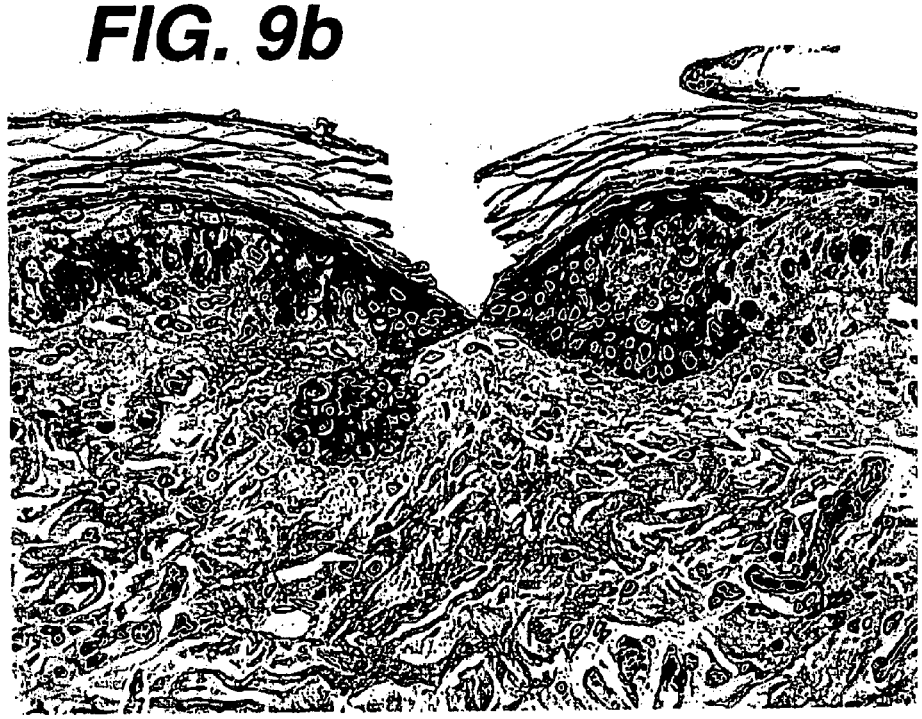

Typical microscopic biopsy results (magnification=220×) of the pig skin treated with electroperforation are shown in FIG. 9. FIG. 9a shows a pore (~64 micrometers) created by electroperforation through the stratum corneum 10 with a minimal damage to the underlying living epidermis 20. FIG. 9b shows a pore that perforated through both stratum corneum 10 and living epidermis 20, but not dermis 30. These results show the flexibility of the electroperforation process of the present invention. Desired depths of tissue perforation may be achieved with the modification of the power and duration of the electric current. For example, stratum corneum perforation may be suitable for transdermal drug delivery, while perforation through the epidermis, or even some part of dermis, may be suitable for interstitial fluid sampling or vaccination.

Transepidermal water loss (TEWL) was also measured on the skin site of electroperforation with Evaporimeter® EP1 (Servomed AB, Stockholm, Sweden). Four measurements were made for each condition. TEWL measurement is well-known in the field of transdermal drug delivery and cosmetic industry as a good indicator for stratum corneum integrity. An increase in TEWL value implies disrupted stratum corneum.

In this experiment, TEWL measurements were conducted as a function of the pores created on the pig skin. We found that as the number of the pores created by electroperforation increased, the TEWL value increased almost proportionally. This result demonstrates that the electroperforation procedure successfully produced pores across the stratum corneum, through which water molecules escaped from the pig body to the outside. This result further demonstrates that interstitial fluid may be extracted through the pores created by electroperforation, and analyzed for its biological substances for diagnostic purposes. Other techniques such as vacuum may be used to aid the interstitial fluid extraction.

EXAMPLE 2

Electroperforation Followed by Passive Diffusion of Insulin for Transdermal Delivery The electroperforation procedure described in Example 1 was conducted in two pigs with a pore density of 39 pores/cm$^2$ of the skin and subsequently followed by transdermal insulin delivery with passive diffusion. An insulin-containing chamber was immediately placed onto the electroperforation-treated skin. The chamber was made of flexible polyethylene containing 0.5 ml of insulin injection solution (Pork insulin, Molecular Weight≅6000 daltons, 100 U/ml, Regular Iletin® II, Eli Lilly, Indianapolis, Ind.). The contact area of the insulin solution in the chamber to the electroperforation-treated skin was 2.3 cm$^2$. The chamber was affixed to the pig skin with a veterinary silicone adhesive at the rim of the chamber. Blood glucose of the pigs was monitored by obtaining blood samples of the ear vein, which were analyzed using two blood glucose analyzers separately to assure the accuracy (One Touch® Basic, LifeScan, Inc., Milpitas, Calif.). The blood glucose levels in both pigs declined rather quickly from the onset of the insulin delivery experiment. The significant blood glucose reduction (greater than 50% of the basal level) indicates that insulin from the drug-containing chamber indeed passed through the pores on the stratum corneum into the body and entered the systemic blood circulation, resulting in the severe hypoglycemia in these pigs.

EXAMPLE 3

Electroperforation followed by Iontophoresis of Insulin for Transdermal Delivery An electroperforation procedure was conducted in two pigs similar with a pore density of 9 pores/cm$^2$ on the skin and subsequently was followed by transdermal insulin delivery. The purpose of using a lower pore density in this experiment was to examine the effect of pore number (e.g., the extent of the transport pathway available) to transdermal insulin delivery. The same insulin-containing chamber and drug application procedures were used in this experiment as those in the Example 2. However, a steel wire was placed in the insulin-containing chamber to serve as a delivery electrode for iontophoresis. The power source of iontophoresis was a commercial iontophoresis apparatus (Phoresor II™, PM700, Motion Control, Inc., Salt Lake City, Utah). The first 1.5 hours of the delivery experiment was by passive diffusion of insulin only. Iontophoresis of insulin was conducted twice in two 30-minute sections with 4 mA DC current at 1.5 hour and 3 hour, respectively, as indicated by the arrows in FIG. 10. The electric polarity of the conductive electrode was reversed every 5 minutes to prevent pH shifting of the drug solution in the chamber.

Figure 10:
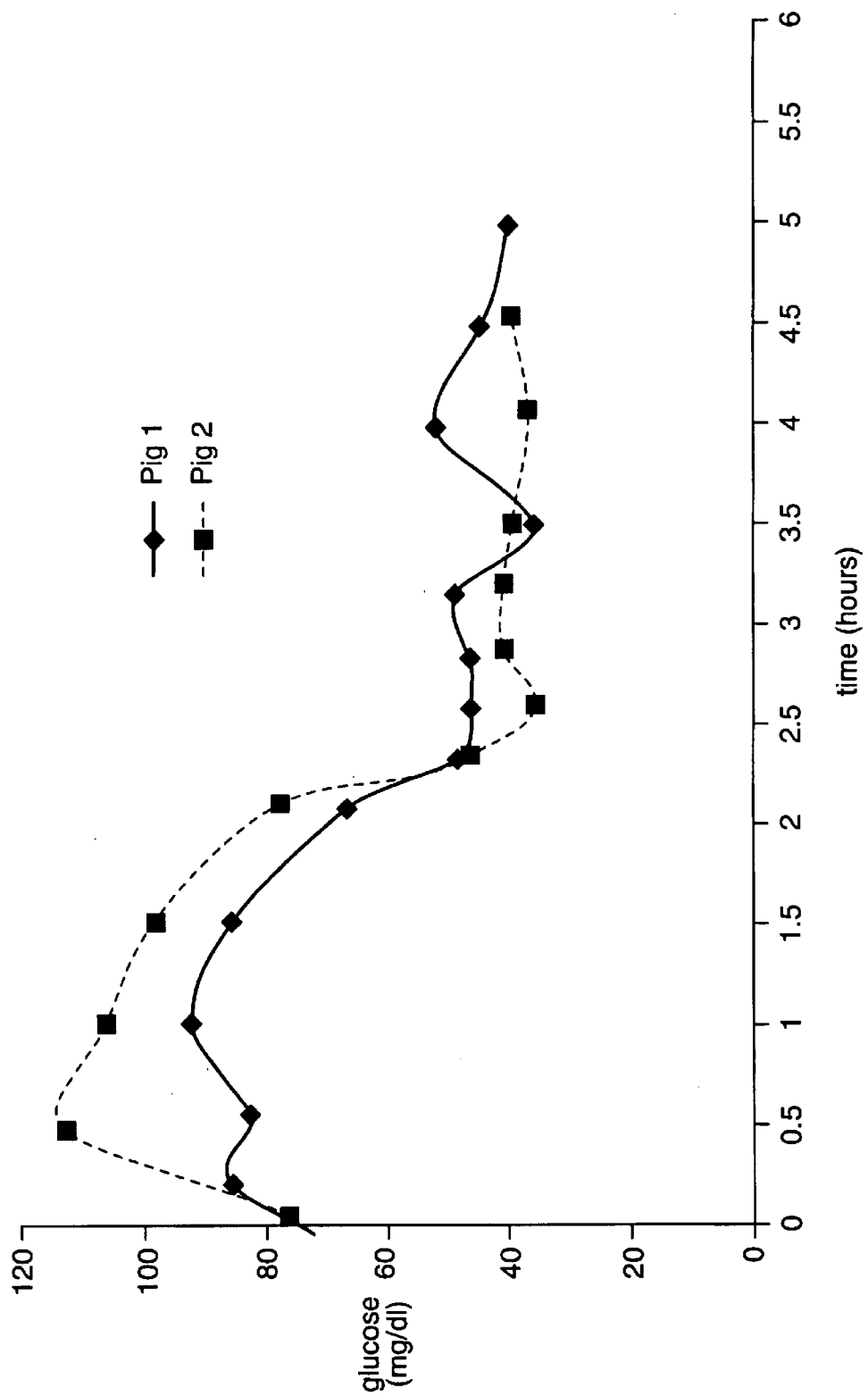
FIG. 10 shows the blood glucose reduction in two pigs as a result from transdermal insulin delivery by iontophoresis through the skin treated with electroperforation.

FIG. 10 shows that the blood glucose levels in both pigs did not decline during the first 1.5 hours of passive diffusion. The result implies that the limited transport pathway available with 9 small pores per cm$^2$ in the stratum corneum might not be enough to deliver insulin and to produce a therapeutically significant blood glucose reduction via passive diffusion (e.g., merely utilizing a concentration gradient). On the other hand, rapid blood glucose reduction during iontophoresis indicates insulin was delivered into the pigs during this time. This result shows that even with limited disruption of stratum corneum, additional driving forces such as iontophoresis can still deliver a macromolecular drug into the skin to exert its therapeutic efficacy.

This result shows the possibility of making a very small transdermal delivery device (e.g., smaller than 1 cm$^2$ or even 0.1 cm$^2$). All the transdermal drug delivery patches currently available are much greater in size (e.g., 10–40 cm$^2$). Such a small size transdermal device would be much more discrete and comfortable for a patient to wear, and would reduce the potential of skin irritation due to skin response to these adhesive-containing devices and prolonged occlusion.

EXAMPLE 4

Electroperforation followed by Passive Diffusion of Erythropoietin for Transdermal Delivery An electroperforation procedure was conducted in two pigs similar to that in Example 3, followed by passive diffusion of erythropoietin (20 kU/ml, Procrit®, Ortho Biotech, Inc., Raritan, N.J.) at the treatment site. There were 25 pores/cm$^2$ generated with electroperforation on each pig. The drug chamber based over the electroperforation-treated skin area contained 0.5 ml of erythropoietin solution. Blood samples were collected for erythropoietin analysis with an ELISA method. The erythropoietin delivery procedure was carried out for 7 hours. The drug-containing chamber was removed at the end of the delivery procedure, but the blood sampling was continued for up to 30 hours following the start of the experiment. It,was found that there was a progressive increase in plasma erythropoietin concentration until the drug-containing chambers were removed from the skin of the pigs. One day after the delivery experiment, the plasma erythropoietin concentrations in the pigs were still above the endogenous basal level It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method for transporting a molecule through a mammalian barrier membrane of at least one layer of cells comprising the steps of:
   creating an air gap between a treatment electrode and said membrane;
   then ablating said membrane with an electric current from said treatment electrode wherein said electric current forms an electric arc within said air gap between said treatment electrode and said membrane; and
   utilizing a driving force to move said molecule through said ablated membrane, wherein said membrane is skin or a mucosal membrane.

2. The method of claim 1, wherein said molecule is a pharmaceutical transported through said membrane into said mammal.

3. The method of claim 2, wherein said pharmaceutical is selected from the group consisting of polysaccharides, peptides, and proteins.

4. The method of claim 1, further comprising the step of applying a conductive material to said membrane prior to said ablation.

5. The method of claim 4, wherein said conductive material is selected from the group consisting of electrolytes, metal particles, and carbon particles.

6. The method of claim 1, wherein the voltage of said electric current is from about 5 to about 2,000 V.

7. The method of claim 1, wherein said method further comprises the use of an indifferent electrode, where said electric current passes from said treatment electrode to said indifferent electrode.

8. The method of claim 1, wherein said electric current comprises a direct current.

9. The method of claim 1, wherein said electric current comprises an alternating current.

10. The method of claim 1, wherein said electric current has a frequency of between about 60 kHz to about 5,000 kHz.

11. The method as in claim 1, wherein the waveform of said electric current is selected from the group consisting of damped sine wave, modulated sine wave, pure sine wave, damped square wave, modulated square wave, pure square wave, direct current and a blend wave thereof.

12. The method of clam 1, wherein said membrane is a mucosal membrane selected from the group consisting of buccal, vaginal, and rectal membranes.

13. The method of claim 1, wherein said membrane is skin.

14. The method of claim 1, wherein said driving force is selected from a group consisting of iontophoresis, electro-osmosis, reverse iontophoresis, electroporation, phonophoresis, pressure gradients, heat and concentration gradients.

15. The method of claim 1, further comprising the step of piercing said membrane with a member selected from the group consisting of needles and blades.

16. The method of claim 1, further comprising the step of cooling said membrane prior to or during said ablation.

17. The method of claim 1, further comprising the step of applying an analgesic to said membrane prior to or during said ablation.

18. The method of claim 1, further comprising the step of monitoring the electrical resistance or impedance of said membrane in order to determine the presence of ablation in said membrane.

* * * * *